|  US007528944B2 |

(12) United States Patent
Chen et al.

(10) Patent No.: US 7,528,944 B2
(45) Date of Patent: May 5, 2009

(54) METHODS AND SYSTEMS FOR DETECTING PINHOLES IN A FILM FORMED ON A WAFER OR FOR MONITORING A THERMAL PROCESS TOOL

(75) Inventors: David Chen, San Jose, CA (US); Andrew Steinbach, Menlo Park, CA (US); Daniel Kavaldjiev, Milpitas, CA (US); Alexander Belyaev, Mountain View, CA (US); Juergen Reich, Campbell, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 14 days.

(21) Appl. No.: 11/751,970

(22) Filed: May 22, 2007

(65) Prior Publication Data
US 2008/0018887 A1    Jan. 24, 2008

Related U.S. Application Data

(60) Provisional application No. 60/747,854, filed on May 22, 2006.

(51) Int. Cl.
*G01N 21/00* (2006.01)
(52) U.S. Cl. ............... 356/237.6; 356/237.1; 356/237.2
(58) Field of Classification Search .... 356/237.1–241.6
See application file for complete search history.

(56) References Cited

U.S. PATENT DOCUMENTS

| 4,162,126 A | * | 7/1979 | Nakagawa et al. | ....... 356/237.2 |
| 4,410,278 A | * | 10/1983 | Makihira et al. | ............ 356/445 |
| 4,845,558 A | | 7/1989 | Tsai et al. | |
| 4,898,471 A | | 2/1990 | Vaught et al. | |
| 5,355,212 A | | 10/1994 | Wells et al. | |

(Continued)

FOREIGN PATENT DOCUMENTS

WO    WO 2006/066135    6/2006

(Continued)

OTHER PUBLICATIONS

U.S. Appl. No. 60/868,769, filed Dec. 6, 2006, Fouquet et al.

(Continued)

*Primary Examiner*—L. G Lauchman
*Assistant Examiner*—Jarreas C Underwood
(74) *Attorney, Agent, or Firm*—Baker & McKenzie LLP

(57) ABSTRACT

Methods and systems for detecting pinholes in a film formed on a wafer or for monitoring a thermal process tool are provided. One method for detecting pinholes in a film formed on a wafer includes generating output responsive to light from the wafer using an inspection system. The output includes first output corresponding to defects on the wafer and second output that does not correspond to the defects. This method also includes detecting the pinholes in the film formed on the wafer using the second output. One method for monitoring a thermal process tool includes generating output responsive to light from a wafer using an inspection system. The output includes the first and second output described above. The wafer was processed by the thermal process tool prior to generating the output. The method also includes monitoring the thermal process tool using the second output.

16 Claims, 8 Drawing Sheets

U.S. PATENT DOCUMENTS

| | | | |
|---|---|---|---|
| 5,555,315 A * | 9/1996 | Itakura | 382/141 |
| 5,625,451 A * | 4/1997 | Schiff et al. | 356/236 |
| 5,909,276 A * | 6/1999 | Kinney et al. | 356/237.2 |
| 5,991,699 A | 11/1999 | Kulkarni et al. | |
| 6,201,601 B1 | 3/2001 | Vaez-Iravani et al. | |
| 6,271,916 B1 | 8/2001 | Marxer et al. | |
| 6,538,730 B2 | 3/2003 | Vaez-Iravani et al. | |
| 6,552,337 B1 * | 4/2003 | Cho et al. | 250/307 |
| 6,596,553 B1 * | 7/2003 | Lin et al. | 438/14 |
| 6,636,031 B1 * | 10/2003 | Kenmochi et al. | 324/158.1 |
| 6,718,526 B1 | 4/2004 | Eldredge et al. | |
| 6,781,688 B2 * | 8/2004 | Kren et al. | 356/237.4 |
| 6,794,885 B1 * | 9/2004 | Yasumoto | 324/557 |
| 6,858,859 B2 | 2/2005 | Kusunose | |
| 6,917,419 B2 | 7/2005 | Fielden et al. | |
| 6,919,957 B2 | 7/2005 | Nikoonahad et al. | |
| 7,006,886 B1 | 2/2006 | Huet et al. | |
| 7,038,773 B2 * | 5/2006 | Kuhlmann et al. | 356/237.4 |
| 7,067,819 B2 | 6/2006 | Janik | |
| 7,286,218 B2 | 10/2007 | Tiemeyer et al. | |
| 7,349,079 B2 | 3/2008 | Zhao et al. | |
| 7,359,052 B2 | 4/2008 | Fielden et al. | |
| 7,369,233 B2 | 5/2008 | Nikoonahad et al. | |
| 7,373,277 B1 * | 5/2008 | Wu et al. | 702/185 |
| 7,417,722 B2 | 8/2008 | Bills et al. | |
| 2002/0182760 A1 | 12/2002 | Wack et al. | |
| 2003/0011786 A1 | 1/2003 | Levy et al. | |
| 2003/0210393 A1 * | 11/2003 | Vaez-Iravani et al. | 356/237.4 |
| 2005/0094864 A1 * | 5/2005 | Xu et al. | 382/145 |
| 2005/0186670 A1 * | 8/2005 | Oh | 435/287.2 |
| 2005/0252752 A1 | 11/2005 | Fielden et al. | |
| 2006/0062445 A1 | 3/2006 | Verma et al. | |
| 2006/0181700 A1 | 8/2006 | Andrews et al. | |
| 2006/0192948 A1 | 8/2006 | Judell et al. | |
| 2006/0192949 A1 | 8/2006 | Bills et al. | |
| 2006/0192950 A1 | 8/2006 | Judelle et al. | |
| 2006/0256326 A1 | 11/2006 | Bills et al. | |
| 2007/0024998 A1 | 2/2007 | Bills et al. | |
| 2007/0156379 A1 | 7/2007 | Kulkarni et al. | |
| 2007/0252977 A1 | 11/2007 | Judell et al. | |
| 2007/0288219 A1 | 12/2007 | Zafar et al. | |
| 2008/0013083 A1 | 1/2008 | Kirk et al. | |

FOREIGN PATENT DOCUMENTS

| | | |
|---|---|---|
| WO | WO 2006/066136 | 6/2006 |
| WO | WO 2006/066137 | 6/2006 |
| WO | WO 2006/066138 | 6/2006 |
| WO | WO 2006/066139 | 6/2006 |
| WO | WO 2006/066205 | 6/2006 |
| WO | WO 2006/066206 | 6/2006 |
| WO | WO 2006/066207 | 6/2006 |
| WO | WO 2006/066255 | 6/2006 |

OTHER PUBLICATIONS

U.S. Appl. No. 60/870,724, filed Dec. 19, 2006, Kulkarni et al.
U.S. Appl. No. 60/883,617, filed Jan. 5, 2007, Park et al.
U.S. Appl. No. 11/680,152, filed Feb. 28, 2007, Chen et al.
U.S. Appl. No. 11/683,696, filed Mar. 8, 2007, Chen et al.
U.S. Appl. No. 11/830,485, filed Jul. 30, 2007, Kulkarni et al.
U.S. Appl. No. 11/855,573, filed Sep. 14, 2007, Wu et al.
U.S. Appl. No. 11/855,581, filed Sep. 14, 2007, Wu et al.
McMillan, Wayne; "Surfscan SP2: Enabling Cost-Effective Production and the 65nm Node and Beyond," Yield Management Solutions, Summer 2004, pp. 14-23.
Larson, C. Thomas; "Measuring Haze on Deposited Metals with Light-Scattering-Based Inspection Systems," MICRO (Sep. 1996), pp. 31-38.
Stover, John C. Optical Scattering: Measurement and Analysis, SPIE Optical Engineering Press, Bellingham, WA (1995).
Elson et al. "Relationship of the total integrated scattering from multilayer-coated optics to angle of incidence, polarization, correlation length, and roughness cross-correlation properties," J.M. et al. Applied Optics, 22, 3207 (1983).
Scheer, B.W. "Development of a physical haze and microroughness standard," SPIE vol. 2863, pp. 78-95 (1996).
Griffith, J.E. et al.; "Characterization of Scanning Probe Tips for Linewidth Measurement," J. Vac. Sci. Technol. B 9(6), Nov./Dec. 1991, pp. 3586-3589.
Malik, Igor J. et al. "Surface Roughness of Si Wafers: Correlating AFM and Haze Measurements," Semiconductor Silicon/1994: Seventh International Symposium on Silicon Materials Science and Technology, ed. H.R. Huff, W. Bergholz and K. Sumino, The Electrochemical Society, Inc. PV 94-10, Pennington, NJ, 1994, p. 1182.
Marx, Egon et al. "Power spectral densities: A multiple technique study of different Si wafer surfaces," J. Vac. Sci. Technol. B 20(1), Jan./Feb. 2002, pp. 31-41.
International Search Report for PCT/US07/61912 dated Feb. 25, 2008.
Holsteynes et al. "The use of unpatterned wafer inspection for immersion lithography defectivity studies." Apr. 2006.
Nemoto et al. "Impact of Silicon Surface Roughness on Device Performance and Novel Roughness Measurement Method," IEEE/SEMI Advanced Semiconductor Manufacturing Conference, 2007.
Chen et al. "Laser Scattering Correlation with Polysilicon Surface Roughness and Impact on Electical Performance," ISSM 2006.
International Search Report and Written Opinion for PCT/US07/69465 mailed on Sep. 17, 2008.
International Application No. PCT/US05/45781 filed on Dec. 12, 2005.

* cited by examiner

METHODS AND SYSTEMS FOR DETECTING PINHOLES IN A FILM FORMED ON A WAFER OR FOR MONITORING A THERMAL PROCESS TOOL

PRIORITY CLAIM

This application claims priority to U.S. Provisional Application No. 60/747,854 entitled "Methods and Systems for Detecting Pinholes in a Film Formed on a Wafer or for Monitoring and/or Controlling a Thermal Process Tool," filed May 22, 2006, which is incorporated by reference as if fully set forth herein.

BACKGROUND OF THE INVENTION

1. Field of the Invention

This invention generally relates to methods and systems for detecting pinholes in a film formed on a wafer or for monitoring a thermal process tool. Certain embodiments relate to detecting pinholes in a film formed on a wafer using output generated by an inspection system that does not correspond to defects on the wafer.

2. Description of the Related Art

The following description and examples are not admitted to be prior art by virtue of their inclusion in this section.

Fabricating semiconductor devices such as logic and memory devices typically includes processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as integrated circuits. However, as the dimensions of semiconductor devices decrease, inspection becomes even more important to the successful manufacture of acceptable semiconductor devices because smaller defects can cause the device to fail. For instance, as the dimensions of semiconductor devices decrease, detection of defects of decreasing size has become necessary since even relatively small defects may cause unwanted aberrations in the semiconductor devices.

Metrology processes are also used at various steps during a semiconductor manufacturing process to monitor and control the process. Metrology processes are different than inspection processes in that, unlike inspection processes in which defects are detected on a wafer, metrology processes are used to measure one or more characteristics of the wafer that cannot be determined from currently used inspection tools. For example, metrology processes are used to measure one or more characteristics of a wafer such as a dimension (e.g., line width, thickness, etc.) of features formed on the wafer during a process such that the performance of the process can be determined from the one or more characteristics. In addition, if the one or more characteristics of the wafer are unacceptable (e.g., out of a predetermined range for the characteristic(s)), the measurements of the one or more characteristics of the wafer may be used to alter one or more parameters of the process such that additional wafers manufactured by the process have acceptable characteristic(s).

There are, however, a number of disadvantages to using metrology processes and tools to measure one or more characteristics of a wafer for process monitoring and control applications. For example, most metrology tools are relatively slow, particularly compared to inspection systems. Therefore, metrology processes are often performed at one location or a limited number of locations on the wafer such that metrology results may be acquired in a relatively expedient manner. However, many processes used to manufacture semiconductor devices produce wafers that have characteristic(s) that vary across the surface of the wafers. As such, using metrology measurements performed at one location or a limited number of locations on a wafer may not provide sufficient information about the characteristic(s) of the wafers such that the process can be accurately monitored and controlled. Furthermore, using metrology tools to measure characteristics across the wafer for inline monitoring and control applications is not feasible due to the time in which such measurements can be performed. In particular, metrology measurements performed by currently available metrology tools such as surface roughness, resistivity, film thickness, etc. are not suitable for high sampling of wafers for inline monitoring since the measurements will impact (e.g., increase) cycle time in production.

Several types of methods and systems are currently used to detect and analyze pinhole formation in thin films on wafers. For example, pinholes can be detected using electric testing (e-test) of device wafers to identify the functional integrity of the devices. In addition, electrical leakage testing may be conducted using tools such as Quantox tools, which are commercially available from KLA-Tencor, San Jose, Calif., on non-metallic thin films. Pinholes can also be detected using scanning electron microscopy (SEM) to conduct review of thin films to visually identify the formation of pinholes. Furthermore, pinholes may be detected by using atomic force microscopy (AFM) to measure the surface roughness of thin films to visually and quantitatively identify the formation of the pinholes.

Each of the methods and systems described above for pinhole formation detection and analysis has a number of disadvantages. For example, electric testing can only identify pinholes on a failed integrated circuit (IC) device. This test takes place a substantially long time (e.g., weeks) after the pinholes have occurred and after hundreds of processing steps have been performed to fabricate the device. In another example, electrical leakage methods can only detect a symptom of pinhole formation, electrical leakage. However, there can be multiple causes for electrical leakage, and this method does not provide direct identification of pinholes. In addition, SEM methods take a substantial amount of time to perform, which is not economically feasible in a manufacturing environment. SEM can also lead to wafer surface damage due to charging of the wafer surface by the electrons used by the SEM. Furthermore, AFM also takes a substantial amount of time to perform, which is not economically feasible in a manufacturing environment. AFM is also substantially sensitive to operator and environmental variations, which can lead to relatively poor detection accuracy and precision.

Several types of methods and systems are currently used to control process variations inside a thermal process tool. For example, zonal monitoring of furnace temperature can be performed using fixed position thermocouples. In addition, intra wafer furnace temperature monitoring can be performed using specialty test wafers that include integrated temperature sensors and transmitters. Additional zonal control of process gas distribution, flow, and pressure inside a thermal chamber may be performed using gas flow controllers. Furthermore, a film metrology tool (e.g., the Spectra FX tool that is commercially available from KLA-Tencor) can be used to identify film thickness and index of refraction at predefined measuring locations on monitor wafers processed by the thermal process tool. Moreover, AFM can be used to measure the surface roughness of wafers having polysilicon formed thereon processed by the thermal process tool.

There are, however, a number of disadvantages to the currently used systems and methods for controlling process variations inside a thermal process tool. For example, in methods and systems that use thermocouples to perform zonal monitoring of furnace temperature, the temperature sensors are located in fixed positions. Therefore, the temperature sensors cannot accurately detect intra and inter wafer temperature variation. In another example, monitoring furnace temperatures using a wafer that includes temperature sensors is disadvantageous since the test wafers are expensive and have a maximum temperature tolerance that is limited to about 135° C. Intra wafer temperature resolution is also limited by the number of sensors that can be included on the wafer. In addition, a gas flow controller can only monitor the flow of process gases as the gases pass through the dispersion unit of the thermal process tool. Therefore, the gas flow controller cannot directly monitor the impact of process gases on the surface of a monitor wafer inside the thermal chamber. Furthermore, intra wafer sensitivity to furnace temperature variation in systems and methods that use film metrology is limited to the predetermined sampling count and location. Moreover, as noted above, AFM methods take a substantial amount of time to perform, which is not economically feasible in a manufacturing environment. AFM systems are also substantially sensitive to operator and environmental variations, which can lead to relatively poor detection accuracy and precision.

Accordingly, it would be advantageous to develop methods and systems for detecting pinholes in a film formed on a wafer or for monitoring a thermal process tool that do not have one or more of the disadvantages described above.

SUMMARY OF THE INVENTION

The following description of various embodiments of methods and systems is not to be construed in any way as limiting the subject matter of the appended claims.

One embodiment relates to a method for detecting pinholes in a film formed on a wafer. The method includes generating output responsive to light from the wafer using an inspection system. The output includes first output corresponding to defects on the wafer and second output that does not correspond to the defects. The method also includes detecting the pinholes in the film formed on the wafer using the second output.

In one embodiment, each of the pinholes is not detectable as a discrete object using the second output. In another embodiment, the second output includes output responsive to dark field background scattering from the film. In an additional embodiment, the inspection system includes a dark field inspection system. In some embodiments, the light includes background scattered light detected using multiple channels of the inspection system.

In one embodiment, generating the output includes generating the output across substantially an entire surface of the wafer. In one such embodiment, detecting the pinholes includes detecting the pinholes across substantially the entire surface of the wafer.

In one embodiment, detecting the pinholes includes determining one or more power spectral density curves using the second output and detecting the pinholes in the film formed on the wafer using the one or more power spectral density curves. In another embodiment, detecting the pinholes includes determining a background light scattering signature using the second output and detecting the pinholes in the film formed on the wafer using the background light scattering signature.

In some embodiments, the method includes determining one or more parameters of the inspection system that can be used to generate the output such that the second output is sensitive to the pinholes. In another embodiment, detecting the pinholes includes detecting the pinholes in a localized surface area of the wafer using the second output. In one such embodiment, the localized surface area has an area approximately equal to an area of an incident beam of light of the inspection system on the wafer. In another embodiment, detecting the pinholes includes detecting the pinholes in localized surface areas of the wafer using the second output. In one such embodiment, the localized surface areas have areas approximately equal to an area of an incident beam of light of the inspection system on the wafer, and the localized surface areas extend across substantially an entire surface of the wafer.

In one embodiment, the method includes determining one or more characteristics of the pinholes as a function of position on the wafer using the second output. In another embodiment, the method includes identifying one or more characteristics of the pinholes in localized surface areas of the wafer using the second output. In one such embodiment, the localized surface areas extend across substantially an entire surface of the wafer.

In one embodiment, the method includes controlling pinhole formation in the film formed on the wafer by applying a threshold to the second output. In another embodiment, the method includes controlling pinhole formation in the film formed on the wafer by determining one or more characteristics of the pinholes in the film formed on the wafer using the second output and applying one or more thresholds to the one or more characteristics.

Each of the steps of each of the embodiments of the method described above may be further performed as described herein. Each of the embodiments of the method described above may include any other step(s) of any other method(s) described herein. In addition, each of the embodiments of the method described above may be performed by any of the systems described herein.

Another embodiment relates to a system configured to detect pinholes in a film formed on a wafer. The system includes an inspection subsystem configured to illuminate the wafer and to generate output responsive to light from the wafer. The output includes first output corresponding to defects on the wafer and second output that does not correspond to the defects. The system also includes a processor configured to detect the pinholes in the film formed on the wafer using the second output. The system described above may be further configured as described herein.

An additional embodiment relates to a method for monitoring a thermal process tool. The method includes generating output responsive to light from a wafer using an inspection system. The output includes first output corresponding to defects on the wafer and second output that does not correspond to the defects. The wafer was processed by the thermal process tool prior to generating the output. The method also includes monitoring the thermal process tool using the second output.

In one embodiment, the second output includes output responsive to dark field background scattering from the wafer. In another embodiment, the inspection system includes a dark field inspection system.

In one embodiment, the monitoring step includes determining one or more characteristics of a surface of the wafer using the second output. In one such embodiment, the one or more characteristics include roughness, granularity, or some combination thereof. In another embodiment, the monitoring step includes determining one or more characteristics of the second output and determining one or more characteristics of a surface of the wafer based on the one or more characteristics of the second output.

In one embodiment, generating the output includes generating the output across substantially an entire surface of the wafer. In one such embodiment, the monitoring step includes determining one or more characteristics of a surface of the wafer across substantially the entire surface of the wafer. In another embodiment, the monitoring step includes determining within wafer variation in one or more characteristics of a surface of the wafer using the second output. In an additional embodiment, the monitoring step includes determining wafer-to-wafer variation in one or more characteristics of surfaces of the wafer and at least one additional wafer using the second output generated for the wafer and the at least one additional wafer.

In one embodiment, the method includes determining one or more correlations between one or more parameters of the thermal process tool and the second output. In another embodiment, the monitoring step includes determining one or more parameters of the thermal process tool corresponding to the second output. In an additional embodiment, the monitoring step includes determining one or more characteristics of a surface of the wafer using the second output and determining one or more parameters of the thermal process tool corresponding to the one or more characteristics of the surface of the wafer. In a further embodiment, the monitoring step includes quantifying one or more changes in one or more characteristics of a surface of the wafer using the second output and identifying one or more magnitudes of the one or more changes due to one or more parameters of the thermal process tool.

In one embodiment, the monitoring step includes determining one or more characteristics of a localized surface area of the wafer using the second output. In one such embodiment, the localized surface area has an area approximately equal to an area of an incident beam of light of the inspection system on the wafer. In another embodiment, the monitoring step includes determining one or more characteristics of localized surface areas of the wafer using the second output. In one such embodiment, the localized surface areas have areas approximately equal to an area of an incident beam of light of the inspection system on the wafer, and the localized surface areas extend across substantially an entire surface of the wafer. In an additional embodiment, the monitoring step includes determining one or more characteristics of individual pixels on the wafer using the second output. In one such embodiment, the individual pixels extend across substantially an entire surface of the wafer.

In one embodiment, the monitoring step includes determining one or more characteristics of a surface of the wafer as a function of position on the wafer using the second output. In one such embodiment, the monitoring step also includes determining variation in one or more parameters of the thermal process tool as a function of the position on the wafer using the one or more characteristics. In another embodiment, the monitoring step includes identifying one or more defects of a surface of the wafer using the second output. In one such embodiment, the one or more defects are caused by variation in one or more parameters of the thermal process tool.

In one embodiment, the method includes performing generating the output for more than one wafer processed simultaneously by the thermal process tool. In one such embodiment, the monitoring step includes determining variation in one or more parameters of the thermal process tool as a function of position of the more than one wafer within the thermal process tool during processing using the second output generated for the more than one wafer.

In one embodiment, the method includes controlling the thermal process tool using the second output. In another embodiment, the method includes controlling one or more parameters of the thermal process tool by applying a threshold to the second output. In an additional embodiment, the method includes controlling one or more parameters of the thermal process tool by determining one or more characteristics of a surface of the wafer using the second output and applying one or more thresholds to the one or more characteristics. In a further embodiment, the method includes controlling one or more parameters of the thermal process tool across substantially an entire processing zone of the thermal process tool using the second output.

Each of the steps of each of the embodiments of the method described above may be further performed as described herein. Each of the embodiments of the method described above may include any other step(s) of any other method(s) described herein. In addition, each of the embodiments of the method described above may be performed by any of the systems described herein.

A further embodiment relates to a system configured to monitor a thermal process tool. The system includes an inspection subsystem configured to illuminate a wafer and to generate output responsive to light from the wafer. The output includes first output corresponding to defects on the wafer and second output that does not correspond to the defects. The wafer was processed by the thermal process tool prior to generation of the output by the inspection subsystem. The system also includes a processor configured to monitor the thermal process tool using the second output. The system described above may be further configured as described herein.

BRIEF DESCRIPTION OF THE DRAWINGS

Other objects and advantages of the invention will become apparent upon reading the following detailed description and upon reference to the accompanying drawings in which.

Figure 1:
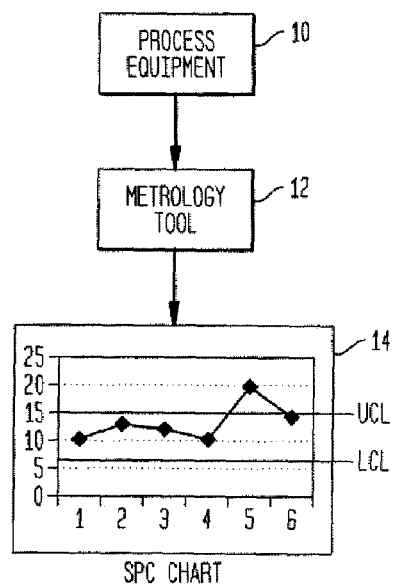
FIG. 1 is a flow chart illustrating one example of a method for monitoring a process based on a characteristic of a wafer.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, and a conductive material. Many different types of such layers are known in the art, and the term wafer as used herein is intended to encompass a wafer including all types of such layers.

One or more layers formed on a wafer may be patterned or unpatterned. In some embodiments, therefore, the wafer includes an unpatterned wafer or a patterned wafer. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

Although the embodiments of the methods and systems are described herein with respect to a wafer, it is to be understood that the methods and systems described herein may be used for determining one or more characteristics of any specimen that is fabricated using a process for which process monitoring and control based on the characteristic(s) is desirable.

As used herein, the term "characteristic" of a wafer refers to a non-defect related characteristic of a wafer that has a value that is normally measured using a metrology tool. In addition, although the characteristic may have a value that is outside of some predetermined limit thereby rendering the wafer "defective," the characteristic is not related to information about defects that can be determined by an inspection system such as the presence of defects, the location of defects, the number of defects, etc. In other words, a characteristic of a wafer as defined herein is not related to point defects on a wafer, which are normally detected by wafer inspection systems. Examples of "characteristics" of a wafer include, but are not limited to, roughness (e.g., of a surface of the wafer or a film formed on the wafer), reflectivity (e.g., of the wafer or a film formed on the wafer), thickness (e.g., of a film formed on the wafer), thickness uniformity or variation (e.g., of a film such as a dielectric film formed on the wafer), polish uniformity (e.g., of a film formed on the wafer), polish slurry residue (i.e., cleanliness of polishing), resistivity (e.g., of a film formed on the wafer), or grain size (e.g., of a polysilicon film formed on the wafer).

The terms "first output" and "second output" are used herein to differentiate between different portions of output generated by an inspection system. The terms "first" and "second" are not used to indicate temporal, spatial, or preferential characteristics of the output.

Turning now to the drawings, it is noted that the figures are not drawn to scale. In particular, the scale of some of the elements of the figures is greatly exaggerated to emphasize characteristics of the elements. It is also noted that the figures are not drawn to the same scale.

Elements shown in more than one figure that may be similarly configured have been indicated using the same reference numerals.

FIG. 1 illustrates one example of a method for monitoring a semiconductor fabrication process. As shown in FIG. 1, the method includes processing a wafer using process equipment 10. Process equipment 10 may include any appropriate process equipment known in the art of semiconductor manufacturing such as a lithography tool, an etch tool, a chemical-mechanical polishing (CMP) tool, a deposition tool (e.g., a chemical vapor deposition (CVD) tool, a physical vapor deposition (PVD) tool, an atomic layer deposition tool, etc.), a cleaning tool, a plating tool, an ion implantation tool, and a thermal tool (e.g., a rapid thermal annealing tool).

After a wafer has been processed by process equipment 10, one or more characteristics of the wafer are measured by metrology tool 12. Metrology tool 12 may include, for example, an atomic force microscope (AFM) or other scanning probe microscope (SPM) that can be used to measure a characteristic such as surface roughness of the wafer or a film formed on the wafer, a metrology tool such as a spectroscopic ellipsometer configured to measure one or more characteristics such as thickness, thickness uniformity, and reflectivity of a thin film formed on the wafer, and a metrology tool configured to measure one or more electrical characteristics such as resistivity of a thin film formed on the wafer.

After the characteristic(s) of the wafer are measured by metrology tool 12, the measured values of the characteristic(s) can be used for process monitoring and control (e.g., statistical process control (SPC)). For instance, the measured value of a characteristic can be plotted in SPC chart 14. The SPC chart illustrates the value of the characteristic as a function of the measurement number or measurement time, which is illustrated by the dotted line in SPC chart 14. The SPC chart also shows the upper control limit (UCL) and the lower control limit (LCL) for the values of the characteristic. The UCL and the LCL may be determined, for example, based on the design of the devices being formed on the wafer and the degree to which variation in the characteristic affects the devices. SPC chart 14, therefore, provides a graphical representation of variation in the characteristic of the wafer that can be used by engineers or operators in a semiconductor fabrication facility to visually monitor the variation in the characteristic. In addition, SPC can be performed automatically using the characteristic(s) measured by metrology tool 12 with or without generating SPC chart 14.

The method shown in FIG. 1 has proven to be useful for process control and monitoring. For example, many characteristics or "physical quantities" of wafers (surface roughness, reflectivity, film measurement, etc.) used for SPC are measured by metrology tools whose ability to measure the physical quantities has been well established to a certain accuracy.

There are, however, a number of disadvantages to the method shown in FIG. 1. In particular, using measurements of one or more characteristics of wafers performed by a metrology tool for process monitoring and control is disadvantageous because such measurements typically take a relatively long time. Therefore, metrology measurements such as those described above are often not suitable for high sampling of wafers for inline monitoring applications without impacting (e.g., increasing) the cycle time in production. As such, monitoring semiconductor fabrication processes using such measurements may reduce the overall throughput of the processes.

Furthermore, to reduce the effects of the time required for such measurements on the cycle time and throughput of the processes, the measurements are typically performed at only one location or a limited number of locations on the wafer. For example, a critical dimension (CD) measurement may be performed by a metrology tool such as a scanning electron microscope (SEM) at only one spot on the wafer. Performing such measurements across substantially an entire surface of the wafer, however, is generally not an option because the time in which such measurements can be performed is simply too long to be practical. However, as is known in the art, the characteristics of a wafer can vary (sometimes greatly) across the surface of the wafer. As such, performing metrology measurements at only one location or a limited number of locations on the wafer may produce measurements that are not representative of the actual performance of the process, which can lead to inaccurate processing monitoring and control.

The alternatives that are available for decreasing the monitoring frequency of physical quantities of wafers by metrology tools include reducing the number of measurements performed by the metrology tools, simply not performing the measurements using the metrology tools, and monitoring a diagnostic parameter of a process tool or process equipment instead of using a metrology tool for process monitoring and control. Obviously, each of these alternatives also are disadvantageous for a number of reasons including decreased process monitoring and control capability and less accurate process monitoring and control.

The method and system embodiments described herein, however, can be used to eliminate one or more of these disadvantages. For example, the method and system embodiments described herein can be used to determine a characteristic of a wafer across substantially an entire surface of the wafer (or at least a relatively large portion of the surface of the wafer) relatively quickly. In particular, the method and system embodiments described herein use inspection techniques such as laser- and scattering-based inspection techniques as a proxy for metrology measurements (e.g., surface roughness measurements, reflectivity measurements, thickness measurements, and any other measurements of characteristics described herein). In this manner, the method and system embodiments described herein can advantageously be used for inline process monitoring and control.

In one such example, inline monitoring of a semiconductor fabrication process at production throughput can be achieved using inspection such as laser scattering inspection and correlating the physical quantity or characteristic of the wafers with the output of the inspection system. Therefore, the method and system embodiments described herein allow the use of an inspection system such as the SPx (e.g., SP1 and SP2) systems that are commercially available from KLA-Tencor, San Jose, Calif., as a metrology proxy thereby enabling higher throughput and approximately 100% measurement coverage of the wafer area for physical quantity monitoring. Furthermore, as the number of different films used in semiconductor device manufacturing increases and as the dimensions of semiconductor devices decrease, the surface roughness of the films becomes an important characteristic for monitoring and controlling the process. Therefore, inline monitoring of such characteristics of wafers by the method and system embodiments described herein will only become more important in the future.

The method and system embodiments described herein can also be used to monitor the surface roughness of these films with relatively good accuracy (e.g., with sub-Angstrom surface roughness measurement capability) and relatively high frequency. Relatively high frequency monitoring may involve measuring every wafer in every lot during early development phases of semiconductor manufacturing and may be performed less frequently (e.g., measuring two wafers per lot or two wafers for every four lots) for more mature processes. Obviously, the frequency with which the method and system embodiments described herein are used for inline monitoring and control may be determined based on the semiconductor fabrication process and may be selected by users in a semiconductor fabrication facility.

Figure 2:
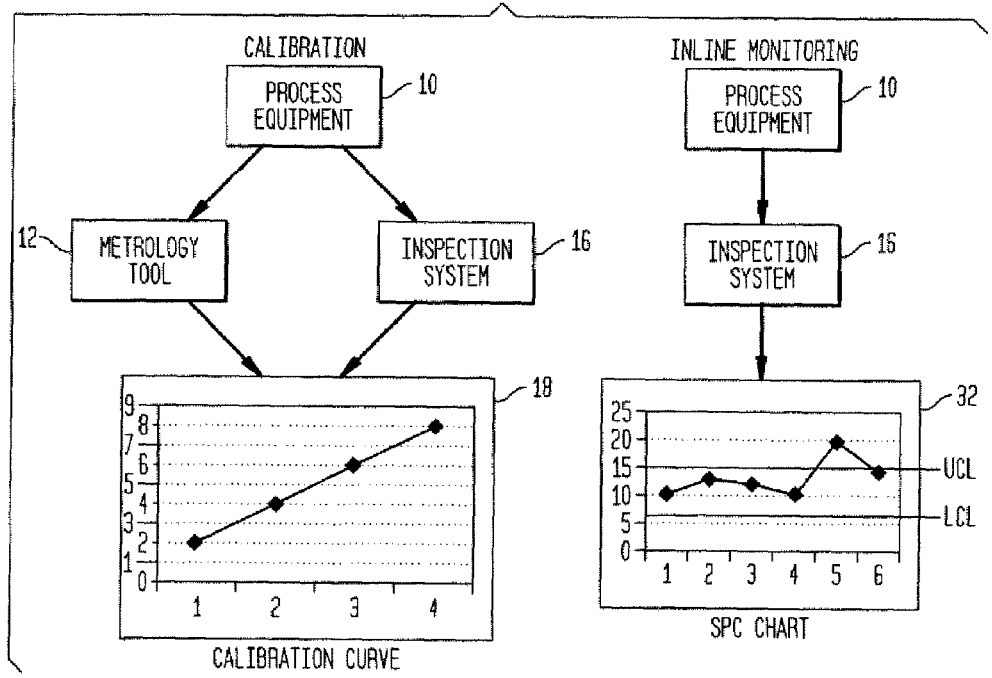
FIG. 2 includes flow charts illustrating one embodiment of a method for setting up a method for monitoring a process based on a characteristic of a wafer and the method for monitoring the process based on the characteristic.

As shown in FIG. 2, one embodiment of a method for setting up (i.e., "calibrating") an embodiment of a method for determining a characteristic of a wafer includes processing a wafer in process equipment 10. Process equipment 10 may include any of the process equipment described above. The method also includes determining one or more characteristics of the wafer using metrology tool 12. Metrology tool 12 may be configured as described above. The one or more characteristics may include any of the characteristic(s) described above. In addition, the method includes generating output responsive to light from the wafer using inspection system 16.

Inspection system 16 may be configured as described herein. For instance, in one embodiment, generating the output using the inspection system includes illuminating the wafer with light produced by a laser. In addition, inspection system 16 may be configured to illuminate the wafer by scanning light across the wafer. In some embodiments, therefore, generating the output using the inspection system includes scanning light across the wafer and generating the output across the wafer. Inspection system 16 may also be configured to detect light scattered from the wafer. In one embodiment, the light from the wafer includes diffusely scattered light.

In an additional embodiment, generating the output using the inspection system includes generating the output across substantially an entire surface of the wafer. Therefore, unlike metrology tools such as AFM tools that scan only a relatively small area (e.g., about 25 microns by about 25 microns) on the wafer to measure a characteristic of the wafer such as surface roughness, the inspection systems described herein can scan across the entire surface of the wafer in a relatively short amount of time (e.g., about 30 seconds). In this manner, the method and system embodiments described herein can measure a characteristic across substantially an entire area of a surface of a wafer in a relatively short time (e.g., about 30 seconds) while measuring the characteristic across the same area on the wafer using a metrology tool can take a relatively long time (e.g., years).

Preferably, more than one wafer is measured by both metrology tool 12 and inspection system 16. For example, the value measured by the metrology tool and the output generated by the inspection system for more than one wafer having approximately the same "real" value of the characteristic may be used to increase the accuracy of the values and output used further in the method. In one such example, the value measured by the metrology tool and the output generated by the inspection system for more than one wafer may be used to generate an average value and an average output, respectively. In addition, more than one wafer, each having a different "real" value of the characteristic, may be acquired by processing the wafers in process equipment 10 with one or more different process parameters and measured by metrology tool 12 and inspection system 16.

The data generated by the method may be used to determine a relationship between the characteristic measured by metrology tool 12 and output from inspection system 16. For instance, the method may include generating calibration curve 18 in which the characteristic measured by metrology tool 12 is plotted as a function of the output of inspection system 16. In this manner, the calibration curve illustrates the correlation between the measured characteristic and the output. The calibration curve or any other data structure defining a relationship between the characteristic and the output may be generated and used in the method embodiments described herein. In this manner, the method described above may be performed for calibrating the output of the inspection system with respect to the measurements of metrology tool 12.

Instead of correlating a characteristic of a wafer measured by a metrology tool to output of an inspection system, the method may be used to determine a correlation between one or more parameters of process equipment 10 and output of inspection system 16. For example, such a correlation may be determined by fixing all but one independent parameter of process equipment 10 and correlating the output of the inspection system such as haze measurements to the parameter. Alternatively, the correlation may be determined by allowing multiple process parameters to vary and using the output generated by multiple channels of the inspection system (which may be configured to detect light from a wafer with different characteristics such as polarization, wavelength, spatial characteristics, etc.) to simultaneously correlate multiple outputs of the inspection system such as multiple haze maps against the independent process parameters. The multiple channels of the inspection system may be configured as described further herein.

The method described above for setting up a method for determining a characteristic of a wafer may be performed prior to using the inspection output for determining a metrology type characteristic of a wafer (i.e., at start up). In addition, the method may be calibrated periodically at relatively low frequency to maintain the accuracy of the method for determining the characteristic of the wafer. For example, the calibration may be performed once a month or once a quarter. The wafers that are used to set up the method may also be used for the periodic calibrations.

One embodiment of a method for determining a characteristic of a wafer is also shown in FIG. 2. The method may include processing a wafer in process equipment 10, which may include any of the process equipment described above. The method also includes generating output responsive to light from the wafer using inspection system 16. The output includes first output corresponding to defects on the wafer and second output that does not correspond to the defects. In particular, if defects are present on the wafer, the defects may alter the portion of the output generated by the inspection system at the positions of the defects.

Figure 3:
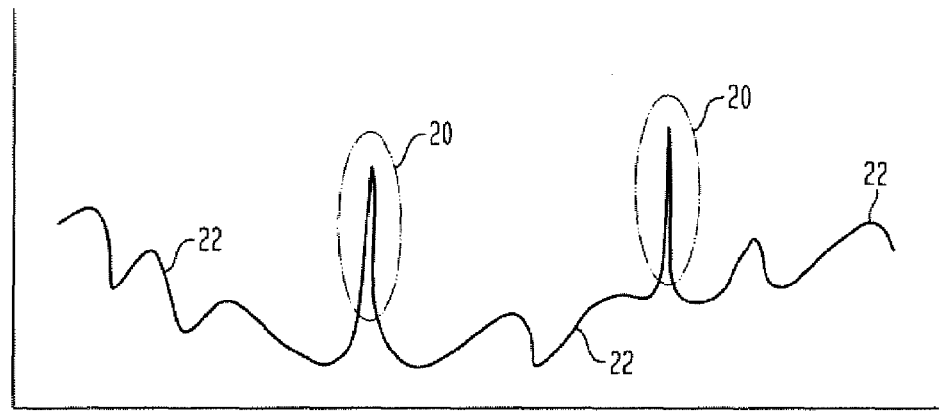
FIG. 3 is a plot illustrating one example of output responsive to light from a wafer generated by an inspection system.

For instance, FIG. 3 illustrates a plot of an example of output of an inspection system (e.g., the wafer surface scattering signal is plotted as a function of position on the wafer). As further shown in FIG. 3, output of an inspection system includes first output 20 corresponding to defects such as particulate defects on the wafer. First output 20 may be identified by applying a threshold or other algorithm to the output. For instance, the output may be compared to a relatively high threshold such that output corresponding to defects can be discriminated from output that corresponds to noise or light scattered from the surface of the wafer. The output also includes second output 22 that includes all of the output that does not correspond to the defects.

The output of the inspection system, therefore, may include a relatively large amount of data for a wafer. Normally, the output corresponding to the defects is the output of interest for inspection, and the output that does not correspond to defects is considered noise, nuisance, or background. For example, the output corresponding to the defects may be stored and further processed (e.g., to form a defect map such as a light point defect (LPD) map, to determine locations of the defects on the wafer, etc.). All other output generated by the inspection system is considered noise for the purposes of inspection and may be discarded since it does not correspond to defects. Much work in the inspection field has been devoted to suppressing the output that does not correspond to defects to increase the sensitivity of defect detection. In the embodiments described herein, however, this second output may be used as a proxy for a characteristic of the wafer. In particular, in the method and system embodiments described herein, this "noise" in the output is used to determine a characteristic of a wafer. In this manner, unlike most methods and systems that are designed to suppress this noise in the output, the method and system embodiments described herein advantageously use this noise as a proxy for a characteristic of the wafer. In other words, output responsive to the light scattered from the surface of the wafer may be acquired and sampled in some manageable way such that it can be processed as described further herein. Furthermore, determining the characteristic using only the second output instead of all of the output of the inspection system increases the accuracy with which the characteristic is determined.

The method also includes determining the characteristic of the wafer using the second output. In one embodiment, determining the characteristic of the wafer includes determining the characteristic of the wafer using the second output and a predetermined correlation between the second output and the characteristic. For example, if "scalibration" is performed as shown in FIG. 2, the characteristic of the wafer may be determined using the second output in combination with calibration curve 18. Therefore, when determining a characteristic of a wafer using an inspection system such as a laser scattering inspection system, the measurements of the inspection system may be reported in physical units such as roughness in Angstroms, sheet resistance in Ohms, and film thickness in Angstroms instead of the typical manner in which measurements performed by inspection systems are reported (e.g., scattering units such as ppm or "total integrated scatter signal") for inspection applications.

Therefore, as shown by comparing the methods of FIGS. 1 and 2 for determining a characteristic of a wafer, the method of FIG. 2 uses output of an inspection system as a metrology proxy for measurements that are normally performed by a metrology tool. Since the characteristic or physical quantity of the wafer can be determined using an inspection system and an appropriate correlation or other data processing described further herein and since inspection systems can acquire data for a wafer much quicker than a metrology tool, the methods and systems described herein can measure the physical quantity of the wafer much faster than traditional metrology equipment. In addition, unlike other methods that have been attempted for indirectly measuring a characteristic of a wafer (e.g., determining a surface roughness from a haze measurement) that involve relatively time consuming and complicated modeling, the method and system embodiments described herein can determine the characteristic of the wafer from a relatively simple correlation or calibration of the output and the characteristic.

As described above, generating the output using the inspection system may include generating the output across substantially an entire surface of the wafer. In one such embodiment, determining the characteristic includes determining the characteristic using the second output generated across substantially the entire surface of the wafer. In this manner, the characteristic may be determined using all of the output generated for the wafer by the inspection system except for the output corresponding to the defects. As such, the characteristic of the wafer may be measured across substantially an entire surface of the wafer.

In another embodiment, determining the characteristic includes determining a value for the second output across an area on the wafer and determining the characteristic from the value. In one such embodiment, the area on the wafer across which the second output is generated and used to determine the value may be substantially an entire area of a surface on the wafer. In this manner, the value may be determined using all of the output generated for the wafer by the inspection system except for the output corresponding to the defects. The value determined for the second output may include, for example, an average, a mean, a median, a standard deviation or any other appropriate value for the second value. In this manner, the characteristic of the wafer determined by this value may be an average, a mean, a median, a standard deviation, etc. of the characteristic. However, such values of the characteristic across an area on the wafer (e.g., substantially an entire area of a surface of the wafer) may be determined in any other manner.

In an additional embodiment, determining the characteristic of the wafer includes determining variation in the second output across the wafer and determining the characteristic from the variation. In a further embodiment, determining the characteristic includes generating a two-dimensional map of the second output across substantially an entire surface of the wafer and determining the characteristic from the two-dimensional map. In other words, the second output generated by the inspection system provides a volume of data that can be used to generate a graphical representation that illustrates the entire wafer and the variation in the characteristic across the wafer. In this manner, the two-dimensional map of the second output may be used to identify surface anomalies of interest (AOI).

In some embodiments, determining the characteristic includes determining a value for the second output across different areas on the wafer and determining the characteristic for the different areas using the values. In another embodiment, determining the characteristic includes determining a single value of the characteristic for different areas on the wafer. In this manner, the method and system embodiments described herein can use the output of an inspection system to find spatial variation in a characteristic of a wafer.

Figure 4:
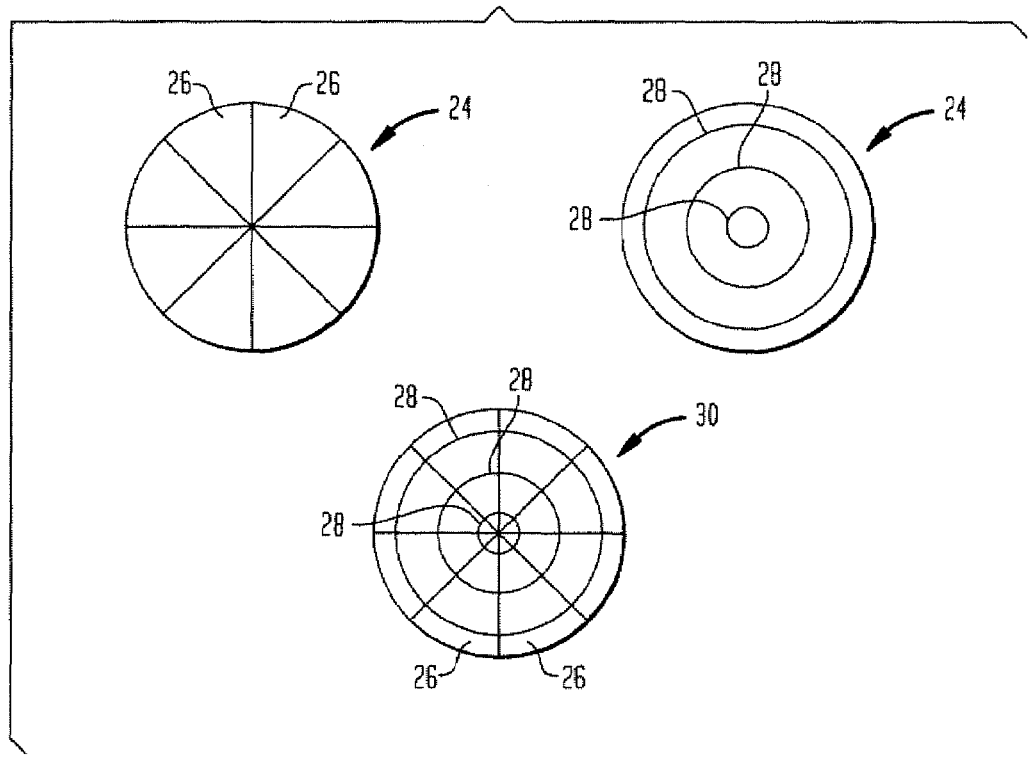
FIG. 4 is a schematic diagram illustrating a top view of various embodiments of different areas on a wafer.

The different areas on the wafer may be defined by different polar coordinates. Examples of such different areas are shown in FIG. 4. In particular, the area of wafer 24 may be divided into different areas 26 that are defined by different angular coordinates or different fixed angles. Substantially the entire area of a surface of wafer 24 may be included in different areas 26, or different areas 26 may span only a portion of the entire surface of the wafer. Although a particular number of different areas 26 are shown in FIG. 4, it is to be understood that the wafer area may be separated into any suitable number of such different areas.

Alternatively, the different areas on the wafer may be defined by different radial coordinates or different fixed radii. In this manner, the different areas on the wafer may have generally concentric circle shapes. One example of such different areas is shown in FIG. 4. In particular, the area of wafer 24 may be divided into different areas 28. Substantially the entire area of a surface of the wafer may be included in different areas 28, or different areas 28 may span only a portion of the entire surface of the wafer. Although a particular number of different areas 28 are shown in FIG. 4, it is to be understood that the wafer area may be separated into any suitable number of such different areas.

In addition, both different areas 26 and 28 may be defined across the area of a single wafer. For example, as shown in FIG. 4, wafer 30 may be separated into different areas 26 and 28. In this manner, the characteristic of the wafer may be determined across different areas that overlap to some extent on the wafer. Determining the characteristic for the overlapping areas may be advantageous when it is desirable to examine the characteristic for variations in different spatial arrangements across a single wafer.

Each of the different areas is larger than an area of a patterned feature on the wafer. For example, the different areas on the wafer may have lateral dimensions of about 1 micron by about 1 micron. In another example, the different areas on the wafer may have lateral dimensions of about 25 microns by about 25 microns. In this manner, the characteristic may be determined for different areas on the wafer that have sizes that are approximately equal to the size of a reticle field printed on the wafer. The lateral dimensions of all, some, or none of the different areas may be the same or different.

Unlike metrology tools that measure a characteristic of an area on the wafer occupied by a single patterned feature, the value of the characteristic determined by the method and system embodiments described herein may be a value that represents the characteristic across an area on the wafer that is much larger than an area of a patterned feature. As such, the effect of any single patterned feature on the output of the inspection system may be reduced or "averaged out." In this manner, unlike metrology tools that are configured to measure a characteristic of a wafer at one or more discrete locations on the wafer, the inspection systems described herein may be used to process the optical characteristics of the wafer (e.g., the second output) on average and to determine the characteristic of the wafer as an average. Therefore, the single value of the characteristic determined for each of the different areas may be an average value of the characteristic across each of the different areas. Accordingly, the characteristics determined by the embodiments described herein are determined on a macro level, while the characteristics of the wafer determined by metrology tools are determined on a micro level.

In a further embodiment, generating the output includes generating the output using multiple channels of the inspection system. In one such embodiment, determining the characteristic includes determining the characteristic using the second output generated by one of the multiple channels. Such an embodiment may also include determining a different characteristic of the wafer using the second output generated by another of the multiple channels. In this manner, by scanning the wafer using an inspection system that has multiple channels, the method and system embodiments described herein can be used to determine multiple characteristics of the wafer. The multiple characteristics may be determined simultaneously. The multiple channels of the inspection system may be configured as described further herein.

The method embodiments described herein may also include detecting defects on the wafer using the output. In particular, as described above, the first output corresponding to defects may be identified in the output generated by the inspection system. The portion of the output that does not correspond to defects may be used as described herein to determine the characteristic of the wafer. Although the first output is not used to determine the characteristic of the wafer, the first output may not be discarded and may, therefore, be used for other purposes. For example, since the first output corresponds to defects and is identified to distinguish the first output from the second output, identifying the first output may also be used to identify and detect defects on the wafer. In this manner, the method and system embodiments described herein may be used to simultaneously detect defects on a wafer and determine a characteristic of the wafer.

As described above, the method embodiments may include generating a two-dimensional map of the second output across an area or substantially an entire surface of the wafer. In this manner, the two-dimensional map may represent an "image" of the area of the wafer or substantially the entire surface of the wafer. As described further above, the "image" represents the low frequency components of the total light scattering signal originating from interaction of the laser with the surface or interfacial material characteristics at varying layer thicknesses and optical properties. In some cases, a continuous and extended area defect can be extensive enough to alter this background haze. In this manner, in addition to detecting defects on the wafer from the first output as described above, the "image" allows analysis of the signature (e.g., a haze signature) on the wafer surface to identify continuous or extended area defects on the wafer that may otherwise be easily overlooked. Some channels of an inspection system may be more sensitive to such defects than other channels. For instance, the normal (narrow) channel of the inspection system described further below may be the most sensitive channel of this system for identifying continuous and extended area defects. In this manner, only a portion of the output of the system may be used for detecting such defects. Detecting such defects may be particularly important in applications such as resist coating layer inspection since such defects may represent small variations in the uniformity of the resist coating layer prior to exposure that in turn can lead to subsequent variation in line width due to the variation in the pre-exposure resist coating layer or a missing pattern in the worst case.

The measurements of the inspection system described herein may be used for process excursion monitoring. In addition, the metrology proxy measurements performed by the inspection system may be used for relatively frequent monitoring of the process because these measurements may be performed much quicker than the measurements performed by metrology tools. In one embodiment, the method includes performing SPC using the characteristic. Performing SPC is generally shown in FIG. 2 by SPC chart 32, which may be configured as described above. However, it is to be understood that SPC may be performed in any suitable manner known in the art. In addition, if more than one characteristic of the wafer is determined in the embodiments described herein, one or more of the characteristics of the wafer can be used to perform SPC. In another embodiment, the method includes performing inline monitoring of a semiconductor fabrication process using the characteristic to detect excursions in the semiconductor fabrication process. In one such embodiment, the method includes determining a standard deviation of the second output for different areas on the wafer and determining if the standard deviations indicate an excursion in a process used to form the wafer.

If a process excursion is identified by the method and system embodiments described herein, the method and system embodiments may identity the wafer on which the process excursion was detected as a candidate for metrology. In this manner, the characteristic of a wafer on which a process excursion was detected may be verified or measured using a metrology tool, and the value of the characteristic determined by the metrology tool may be used to determine the appropriate correction for the process.

In some embodiments, the method includes determining variation in the second output across the wafer and determining if the variation is associated with a signature of a process tool used to form the wafer. For example, a wafer that has been processed by a deposition tool may have a characteristic that varies across the wafer due to the chuck of the deposition tool. In addition, the variation in the characteristic of the wafer due to the chuck may be detected using the output (e.g., haze measurements) of the inspection system. The variation in the second output may be determined as a standard deviation in the second output. In addition, the standard deviation in the second output may be determined for different areas on the wafer. The different areas may be defined as described further herein. The standard deviations for each of the different areas may be compared to a predetermined threshold or limit for the standard deviation. In this manner, the standard deviation values that are greater than the threshold or limit may be flagged or identified as indicating a process excursion that may be associated with the signature of the process tool.

In a further embodiment, the method includes generating a two-dimensional map of the second output across substantially an entire surface of the wafer, determining if an abnormal pattern is present in the two-dimensional map, and if an abnormal pattern is present, determining if the abnormal pattern corresponds to an excursion in a process used to form the wafer. The abnormal patterns in the two-dimensional map may be identified using any suitable method and/or algorithm known in the art. The abnormal patterns that can be detected using such a method include, but are not limited to, a chuck imprint of a deposition tool (e.g., a CVD deposition tool), poor or non-uniform etch, a "swirl" in copper formed by an electro-chemical deposition (ECD) process, a pattern corresponding to a showerhead of a plasma CVD tool that uses tetraethoxy silane (TEOS) gas, thickness variation, wet cleaning problems, and slurry residue. In this manner, the method and system embodiments described herein may be used to identify spatial variation in a characteristic of a wafer and to use the spatial variation as an indicator of process excursions.

The method may also include storing results of the determining step in a storage medium. The results of the determining step may include any of the results described herein. In addition, the storing step may include storing results of the determining step in addition to any other results of any steps of any method embodiments described herein. The results may be stored in any manner known in the art. In addition, the storage medium may include any storage medium described herein or any other suitable storage medium known in the art. After the results have been stored, the results can be accessed in the storage medium and used by any of the method or system embodiments as described herein. Furthermore, the results may be stored "permanently," "semi-permanently," temporarily, or for some period of time. For example, the storage medium may be random access memory (RAM), and the results of the selecting step may not necessarily persist indefinitely in the storage medium.

Figure 5:
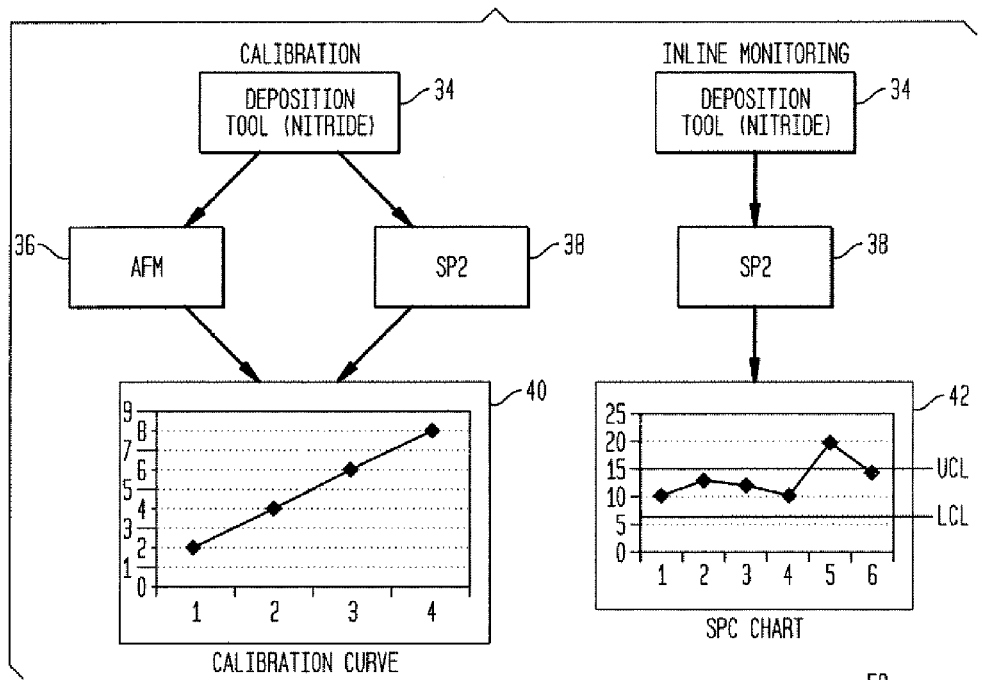
FIG. 5 includes flow charts illustrating another embodiment of a method for setting up a method for monitoring a process based on a characteristic of a wafer and the method for monitoring the process based on the characteristic.

FIG. 5 illustrates one particular implementation of an embodiment of a method for setting up a method for determining a characteristic of a wafer and one particular implementation of an embodiment of such a method for determining the characteristic of the wafer. As shown in FIG. 5, setting up the method or "calibration" includes processing one or more wafers in deposition tool 34. Deposition tool 34 may, in this example, be used to form a nitride layer on the one or more wafers. However, deposition tool 34 may be configured to deposit or form any suitable layer known in the art of semiconductor fabrication on the wafer(s). The deposition tool may be used to form the layer having substantially the same characteristics (e.g., thickness) on more than one wafer. In addition, the deposition tool may be used to form layers having different characteristics (e.g., thickness) on more than one wafer.

As shown in FIG. 5, one or more characteristics of wafer(s) processed by deposition tool 34 may be measured by AFM 36. AFM 36 may be used to measure a surface roughness of the nitride or other layer formed on the wafer(s). AFM 36 may include any suitable AFM known in the art, and many suitable AFM systems are commercially available. Wafer(s) processed by deposition tool 34 and measured by AFM 36 are also measured using an inspection system such as SP2 system 38 that is commercially available from KLA-Tencor. However, the inspection system used to measure the wafer(s) may include any suitable inspection system known in the art, and many suitable inspection systems such as the SP1 and AIT family of tools are commercially available from KLA-Tencor. The inspection system may be configured to measure the wafer by generating output responsive to the light from the wafer according to any of the embodiments described herein.

The measurements performed on the wafer(s) by AFM 36 and SP2 system 38 may be analyzed and/or processed to determine a correlation between the different measurements. For example, as shown in FIG. 5, the method may include generating calibration curve 40 that describes a correlation between the measurements of the wafer(s) performed by AFM 36 and SP2 system 38. However, any other suitable data structures (e.g., a look up table, a mathematical function, or an algorithm) may be used to describe the relationship between the measurements performed by AFM 36 and SP2 system 38. In addition, measurements performed on multiple wafers having substantially the same characteristics may be used to create the correlation thereby increasing the accuracy of the correlation. Furthermore, measurements performed on multiple wafers having different characteristics may be used to create the correlation across different possible values of the characteristic(s) thereby increasing the accuracy of the correlation across a range of possible values. The "calibration" of the SP2 system may be performed as shown in FIG. 5 at relatively low frequency (e.g., at start up and for periodic maintenance (PM)). The "calibration" method shown in FIG. 5 may include any other step(s) of any other method(s) described herein.

As further shown in FIG. 5, the method for determining a characteristic of the wafer may be used for inline monitoring. During inline monitoring, wafers may be processed by deposition tool 34 to form a nitride or other suitable layer on the wafers. Wafers on which the nitride or other layer is formed may then be measured by SP2 system 38. Output of the SP2 system in combination with calibration curve 40 or other data structure described above may be used to determine one or more characteristics of the wafers. For example, output of the SP2 system may be used in combination with calibration curve 40 to determine the surface roughness of the layers formed on the wafers.

The characteristic(s) of the wafer determined from the output of the SP2 system and the calibration curve may then be used for SPC of the process performed by deposition tool 34. For example, SPC of the process performed by the deposition tool may be performed by generating SPC chart 42, which may be configured and used as described above. However, SPC of the deposition process may be performed in any suitable manner known in the art. Since the output of the SP2 system can be generated relatively quickly and the characteristic of the wafer can be determined relatively quickly from the output, the method shown in FIG. 5 may be used for relatively frequent monitoring of the deposition process (e.g., daily monitoring). In addition, since the output of the SP2 system can be generated relatively quickly across substantially an entire area of a surface of the wafer, relatively frequent monitoring of the process may be performed using full wafer coverage measurements of the characteristic. The embodiments of the methods shown in FIG. 5 may include any other step(s) of any other method(s) described herein. In addition, the embodiments of the methods shown in FIG. 5 have all of the advantages of the method embodiments described above.

Figure 6:
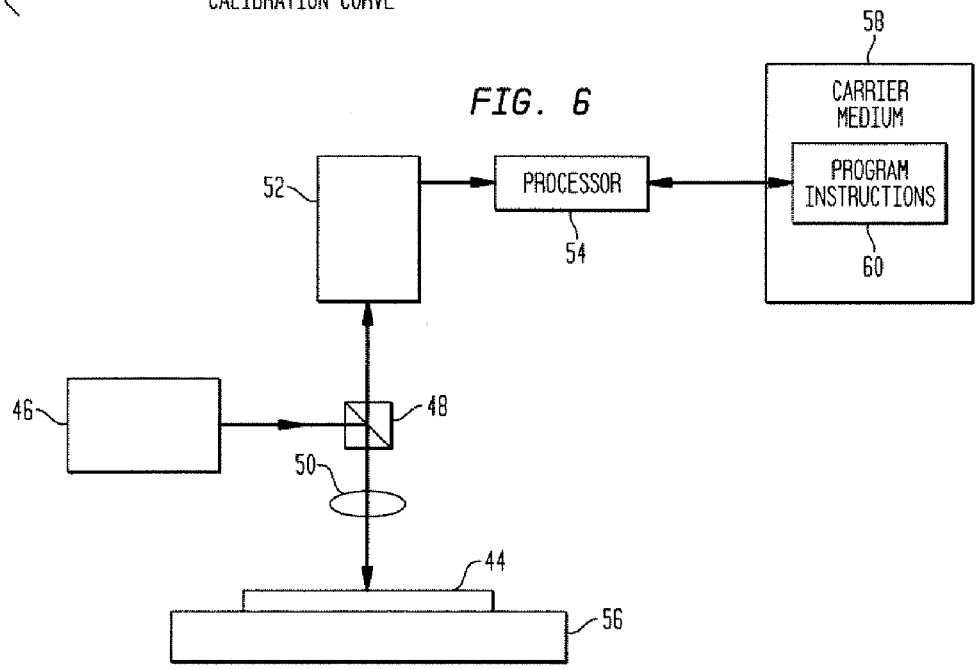
FIGS. 6-7 are schematic diagrams illustrating a cross-sectional view of various embodiments of a system configured to determine a characteristic of a wafer.

FIG. 6 illustrates one embodiment of a system configured to determine a characteristic of a wafer. The system includes an inspection subsystem that is configured to illuminate wafer 44 and to generate output responsive to light from the wafer. The output includes first output corresponding to defects on the wafer and second output that does not correspond to the defects. For example, the inspection subsystem includes light source 46. Light source 46 may include any suitable light source known in the art. Light generated by light source 46 is directed to beam splitter 48. Beam splitter 48 is configured to direct the light generated by light source 46 to objective 50. Objective 50 is configured to focus the light onto wafer 44. In this manner, the light source, beam splitter, and objective of the inspection subsystem are configured to illuminate wafer 44. Beam splitter 48 and objective 50 may include any suitable optical components known in the art. In one embodiment, light source 46 includes a laser. In this manner, the inspection subsystem may be configured to illuminate the wafer with light produced by a laser.

Light specularly reflected from wafer 44 is collected by objective 50, directed by objective 50 to beam splitter 48, and passed through beam splitter 48 to detector 52. Detector 52 may include any suitable detector known in the art. Since light detected by detector 52 includes light specularly reflected from wafer 44, the inspection subsystem shown in FIG. 5 is configured as a bright field inspection subsystem. In addition, since the systems described herein are preferably configured to determine the characteristic of the wafer across a relatively large area on the wafer (e.g., substantially an entire area of a surface of the wafer) for the purposes of process excursion monitoring, the inspection subsystem may be configured to detect the light specularly reflected across a relatively large area on the wafer and at relatively low resolution. In this manner, light source 46, beam splitter 48, and objective 50 may be configured to illuminate a relatively large area or spot on wafer 44. In addition, detector 52 may be a relatively low quality imaging detector or a non-imaging detector capable of measuring only an intensity of the light reflected from the wafer.

The inspection subsystem shown in FIG. 6 may include any other suitable components or devices known in the art. For example, as shown in FIG. 6, the inspection subsystem may include stage 56 on which wafer 44 may be disposed during measurements by the inspection subsystem. Stage 56 may include any suitable mechanical or robotic assembly known in the art. Stage 56 may be configured to move wafer 44 during measurements performed by the inspection subsystem such that the inspection subsystem generates output responsive to light from the wafer by scanning light across the wafer and generating the output across the wafer. In addition, the inspection subsystem may be configured to generate the output responsive to the light from the wafer by generating the output across substantially an entire area of the surface of the wafer.

Detector 52 may generate output that can be used as described further herein. In addition, the output generated by detector 52 may include first output corresponding to defects on wafer 44 and second output that does not correspond to the defects. The system also includes processor 54 configured to determine the characteristic of the wafer using the second output. For example, processor 54 may be coupled to detector 52 in any manner known in the art (e.g., via a transmission medium that may include "wired" and "wireless" portions). In this manner, processor 54 may be configured to receive output generated by detector 52.

Processor 54 may be configured to determine the characteristic of the wafer using the second output generated by detector 52 as described further herein. For example, in one embodiment, processor 54 is configured to determine the characteristic using the output generated across substantially the entire surface of the wafer. In another embodiment, processor 54 is configured to determine the characteristic of the wafer using the second output and a predetermined correlation between the second output and the characteristic. In an additional embodiment, the processor is configured to determine a value for the second output across an area on the wafer and to determine the characteristic from the value. In some embodiments, the characteristic is an average characteristic across an area on the wafer.

In another embodiment, processor 54 is configured to determine variation in the second output across the wafer and to determine the characteristic from the variation. In one such embodiment, the processor may be configured to determine a graininess of a film or films deposited on the wafer by determining if pixels of data in the second output have values that fall into a mean/range space using segmented auto thresholding (SAT) and estimating the graininess of the film from the number of pixels that have such values. In a further embodiment, processor 54 is configured to generate a two-dimensional map of the second output across substantially an entire surface of the wafer and to determine the characteristic of the wafer from the two-dimensional map. In some embodiments, processor 54 is configured to determine a value for the second output across different areas on the wafer and to determine the characteristic for the different areas using the values. In an additional embodiment, the processor is configured to determine a single value of the characteristic for different areas on the wafer. Each of the different areas is larger than an area of a patterned feature on the wafer.

Processor 54 may be configured to perform any other step(s) of any other method(s) described herein. For example, in one embodiment, processor 54 is configured to perform SPC using the characteristic. In another embodiment, processor 54 is configured to perform inline monitoring of a semiconductor fabrication process using the characteristic to detect excursions in the process. In some embodiments, processor 54 is configured to determine a standard deviation of the second output for different areas on the wafer and to determine if the standard deviations indicate an excursion in a process used to form the wafer. In a further embodiment, the processor is configured to generate a two-dimensional map of the second output across substantially an entire surface of the wafer, to determine if an abnormal pattern is present in the two-dimensional map, and if an abnormal pattern is present, to determine if the abnormal pattern corresponds to an excursion in a process used to form the wafer. In an additional embodiment, the processor is configured to detect defects on the wafer using the output. Each of the steps described above may be performed by the processor as described further herein.

Processor 54 may take various forms, including a personal computer system, mainframe computer system, workstation, image computer, parallel processor, or any other suitable device known in the art. In general, the term "computer system" may be broadly defined to encompass any device having one or more processors, which executes instructions from a memory medium. The embodiments of the system shown in FIG. 6 have all of the advantages of the methods described above.

In some embodiments, the system shown in FIG. 6 also includes carrier medium 58. Program instructions for implementing methods such as those described herein may be transmitted over or stored on the carrier medium. In particular, carrier medium 58 includes program instructions 60 executable on processor 54 for performing one or more steps of the methods described herein. For example, in one embodiment, carrier medium 58 includes program instructions 60 executable on a computer system such as processor 54 for performing a method for determining a characteristic of wafer 44. Although the processor and carrier medium are shown in FIG. 6 as coupled to an inspection subsystem, it is to be understood that the processor and/or carrier medium may be configured as separate "stand-alone" components. Such stand-alone components may, however, be coupled to an inspection system (e.g., by a transmission medium that may include "wired" and "wireless" portions) such that the components can receive output generated by the inspection system.

The computer-implemented method includes acquiring output responsive to light from the wafer generated by an inspection system. Acquiring the output may be performed by processor 54 as described further above. The output includes first output corresponding to defects on the wafer and second output that does not correspond to the defects. In some embodiments, the method includes identifying the first and second output in the output acquired from the inspection system. The first and second output may be identified as described further above.

The method also includes determining the characteristic of the wafer using the second output. Determining the characteristic of the wafer may be performed as described further herein. For example, in one embodiment, determining the characteristic includes determining the characteristic of the wafer using the second output generated across substantially an entire surface of the wafer. In another embodiment, determining the characteristic includes determining the characteristic of the wafer using the second output and a predetermined correlation between the second output and the characteristic. In an additional embodiment, determining the characteristic of the wafer includes determining a value for the second output across an area on the wafer and determining the characteristic from the value. In some embodiments, the characteristic is an average characteristic across an area on the wafer.

In a further embodiment, the method includes determining variation in the second output across the wafer and determining the characteristic from the variation. In another embodiment, determining the characteristic includes generating a two-dimensional map of the second output across substantially an entire surface of the wafer and determining the characteristic from the two-dimensional map. In some embodiments, determining the characteristic includes determining a value for the second output across different areas on the wafer and determining the characteristic for the different areas using the values. In an additional embodiment, determining the characteristic includes determining a single value of the characteristic for different areas on the wafer. Each of the different areas is larger than an area of a patterned feature on the wafer.

In a further embodiment, the output may be generated by multiple channels of the inspection system. In one such embodiment, determining the characteristic includes determining the characteristic using the second output generated by one of the multiple channels. Such an embodiment may also include determining a different characteristic of the wafer using the second output generated by another of the multiple channels.

The computer-implemented method may include any other step(s) of any other method(s) described herein. For example, in one embodiment, the computer-implemented method includes performing SPC using the characteristic. In another embodiment, the method includes performing inline monitoring of a semiconductor fabrication process using the characteristic to detect excursions in the semiconductor fabrication process. In an additional embodiment, the method includes determining a standard deviation of the second output for different areas on the wafer and determining if the standard deviations indicate an excursion in a process used to form the wafer.

In one embodiment, the computer-implemented method includes determining variation in the second output across the wafer and determining if the variation is associated with a signature of a process tool used to form the wafer. In some embodiments, the method includes generating a two-dimensional map of the second output across substantially an entire surface of the wafer, determining if an abnormal pattern is present in the two-dimensional map, and if an abnormal pattern is present, determining if the abnormal pattern corresponds to an excursion in a process used to form the wafer. In a further embodiment, the computer-implemented method includes detecting defects on the wafer using the output. Each of the steps of the computer-implemented method described above may be performed as described further herein. Each of the embodiments of the computer-implemented method described above has all of the advantages of the methods described above.

The embodiments of the carrier medium may include program instructions executable on a computer system of any other inspection system that is or can be configured as described herein. The carrier medium may be a transmission medium such as a wire, cable, or wireless transmission link. The carrier medium may also be a storage medium such as a read-only memory, a random access memory, a magnetic or image acquisition disk, or a magnetic tape.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Figure 7:
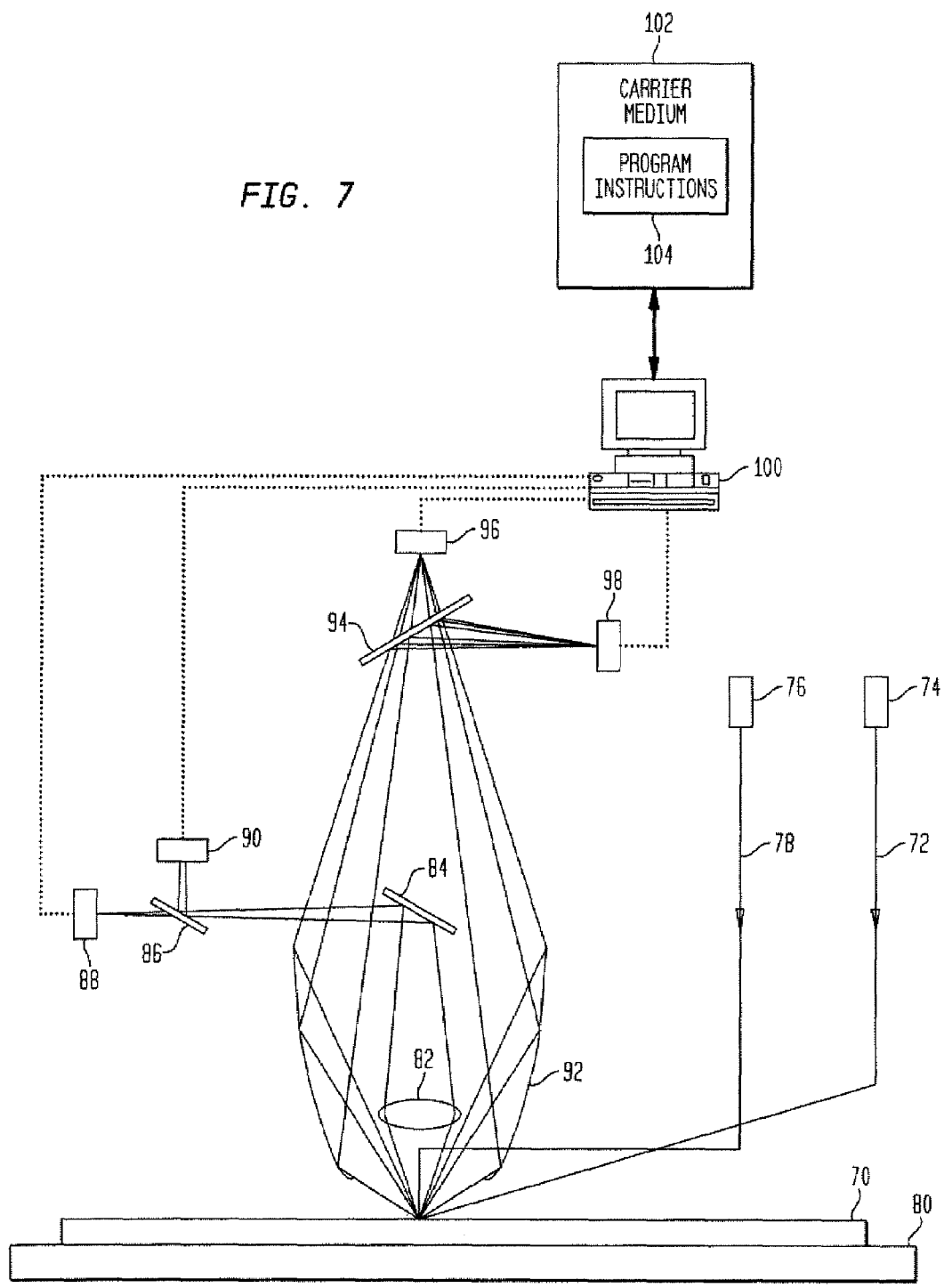

Another embodiment of a system that is configured to inspect a wafer is illustrated in FIG. 7. The system shown in FIG. 7 is configured for unpatterned wafer inspection and is based on the SP1-TBI system, which is commercially available from KLA-Tencor. This inspection system is described in more detail in U.S. Pat. No. 6,538,730 to Vaez-Iravani et al., which is incorporated by reference as if fully set forth herein. The system shown in FIG. 7 may be further configured as described in this patent for patterned and unpatterned wafer inspection. For the sake of clarity, some of the components and details of the system have been omitted from FIG. 7 and the corresponding description presented herein. In addition, U.S. Pat. No. 6,538,730 is related to U.S. Pat. No. 6,201,601 to Vaez-Iravani et al. and U.S. Pat. No. 6,271,916 to Marxer et al., which are also incorporated by reference as if fully set forth herein. The system shown in FIG. 7 may be further configured as described in these patents.

The system shown in FIG. 7 includes an inspection subsystem. The inspection subsystem is configured to illuminate the wafer and to generate output responsive to light from the wafer. The output includes first output corresponding to defects on the wafer and second output that does not correspond to the defects.

The inspection subsystem includes an illumination subsystem. The illumination subsystem may be configured to generate light 72. For instance, the illumination subsystem may include light source 74, which is configured to generate light 72. The illumination subsystem is configured to direct light 72 to wafer 70 at an oblique angle of incidence. The illumination subsystem may include a number of optical components (not shown) positioned in a path of light 72 such as folding mirror(s), beam splitter(s), polarizing component(s), filter(s), and lenses. The oblique angle of incidence may vary depending on, for example, the characteristics of the light and the characteristics of the wafer. One suitable angle of incidence may be about 70° from normal to the upper surface of the wafer.

The illumination subsystem also includes light source 76. Light source 76 is configured to generate light 78, which is directed by the illumination subsystem to wafer 70 at a substantially normal angle of incidence. The illumination subsystem may include a number of optical components (not shown) positioned in the path of light 78. These optical components may include any of those described above.

Light sources 74 and 76 may include any suitable light sources known in the art such as lasers. In one embodiment, therefore, the inspection subsystem is configured to illuminate the wafer with light produced by one or more lasers. In a different embodiment, the system may include a single light source (not shown) that is used to provide light for both oblique and normal illumination as described further above. For example, a single light source such as a multi-wavelength laser may be coupled to a beam splitter (not shown). The beam splitter may be configured to split the light from the laser into separate beams having different wavelengths, one of which is used for normal illumination and the other of which is used for oblique illumination. The illumination subsystem may include any other suitable combination of a single light source and beam multiplier(s) known in the art.

Wafer 70 is supported on stage 80, which may be rotated and translated such that light 72 and 78 illuminates an area or spot on the wafer that moves in a spiral path. Alternatively, light 72 and 78 may be scanned over the wafer in any manner known in the art to trace the spiral path or another type of scan path across the wafer. In this manner, the inspection subsystem may be configured to illuminate the wafer by scanning light across the wafer and to generate the output as described further herein across the wafer. In addition, the inspection subsystem may be configured to scan the light across substantially an entire surface of the wafer and to generate the output as described further herein across substantially the entire surface of the wafer.

Illumination of the wafer will cause scattering of the light from the wafer. In addition, both oblique incidence light and normal incidence light may be scattered from the wafer. The inspection subsystem shown in FIG. 7 includes a detection subsystem that is configured to collect light scattered from the wafer and to generate output responsive to light from the wafer. The output can be used to determine a characteristic of the wafer as described further herein.

The detection subsystem includes lens collector 82, mirror 84, beam splitter 86, and detectors 88 and 90, which form a "narrow" channel of the detection subsystem. In other words, light scattered from the illuminated area on the wafer along directions relatively close to normal to the surface of the wafer is collected and focused by lens collector 82. In this manner, lens collector 82 collects light scattered from the wafer at relatively "narrow" scattering angles. The light from the wafer collected by lens collector 82 may include diffusely scattered light. Lens collector 82 directs the collected light to mirror 84, which directs the light to beam splitter 86. Beam splitter 86 is configured to direct one portion of the light to detector 88 and the other portion of the light to detector 90. One detector may be used to detect light scattered at relatively narrow angles due to illumination by the normal incidence beam, and the other detector may be used to detect light scattered at relatively narrow angles due to illumination by the oblique incidence beam. Detectors 88 and 90 may include any suitable detectors known in the art (e.g., PMTs). In addition, detectors 88 and 90 may be similarly or differently configured. The narrow channel portion of the detection subsystem may include any other optical components (not shown) known in the art. For example, one or more spectral filtering components (e.g., bandpass filters) may be placed in the path of the collected light between beam splitter 86 and each of detectors 88 and 90. In addition, a spatial filter may be included in the narrow channel portion of the detection subsystem to prevent the specular reflection of the normal incidence beam from reaching detectors 88 and 90.

The detection subsystem also includes ellipsoidal mirror 92, beam splitter 94, and detectors 96 and 98, which form a "wide channel" of the detection subsystem. In other words, light scattered from the illuminated area on the wafer along directions relatively far from normal to the surface of the wafer is collected and focused by ellipsoidal mirror 92. In this manner, ellipsoidal mirror 92 collects light scattered from the wafer at relatively "wide" scattering angles. The light from the wafer that is collected by ellipsoidal mirror 92 may include diffusely scattered light. Ellipsoidal mirror 92 directs the collected light to beam splitter 94. Beam splitter 94 is configured to direct one portion of the light to detector 96 and the other portion of the light to detector 98. One detector may be used to detect light scattered at relatively wide angles due to illumination by the normal incidence beam, and the other detector may be used to detect light scattered at relatively wide angles due to illumination by the oblique incidence beam. Detectors 96 and 98 may include any suitable detectors known in the art (e.g., PMTs). In addition, detectors 96 and 98 may be similarly or differently configured. The wide channel portion of the detection subsystem may include any other optical components (not shown) known in the art. For example, one or more spectral filtering components (e.g., bandpass filters) may be placed in the path of the collected light between beam splitter 94 and each of detectors 96 and 98.

Detectors 88, 90, 96, and 98 are configured to generate output responsive to the light scattered from the wafer. Processor 100 is coupled to detectors 88, 90, 96, and 98 by transmission media as shown by the dotted lines in FIG. 7. The transmission media may include any suitable transmission media known in the art. In addition, one or more additional components (not shown) may be interposed between each of the detectors and the processor such as analog-to-digital converters. In this manner, output generated by the detectors can be sent to and received by the processor. The processor is configured to determine a characteristic of the wafer using the output as described further herein.

As described above, the inspection subsystem includes multiple channels (e.g., the wide channel and the normal channel). In this manner, the inspection subsystem may be configured to generate the output using the multiple channels. The multiple channels are configured to detect light with different parameters (e.g., different wavelengths, different angles of incidence, different angles of collection, or some combination thereof). The output of one of the channels may be sensitive to one characteristic of the wafer (e.g., roughness) and another of the channels may be sensitive to another characteristic of the wafer (e.g., thickness). In this manner, the output produced by the different channels of the inspection subsystem may be used independently or separately to determine different characteristics of the wafer. For example, processor 100 may be configured to determine one characteristic of the wafer using the second output generated by one of the multiple channels and to determine another characteristic of the wafer using the second output generated by another of the multiple channels. Processor 100 may be further configured as described herein. The system shown in FIG. 7 may be further configured as described herein. In addition, the system shown in FIG. 7 has all of the advantages of the methods described above.

The system shown in FIG. 7 may also include carrier medium 102. Program instructions for implementing methods such as those described herein may be transmitted over or stored on the carrier medium. In particular, carrier medium 102 includes program instructions 104 executable on processor 100 for performing one or more steps of the computer-implemented methods described herein. For example, in one embodiment, carrier medium 102 includes program instructions 104 executable on a computer system such as processor 100 for performing a method for determining a characteristic of wafer 70. The carrier medium and the program instructions may be further configured as described herein.

In some embodiments, the systems described herein may be configured as "stand alone tools" or tools that are not physically coupled to a process tool. However, such a system may be coupled to the process tool (not shown) by a transmission medium, which may include wired and wireless portions. The process tool may include any process tool known in the art such as a lithography tool, an etch tool, a deposition tool, a polishing tool, a plating tool, a cleaning tool, an ion implantation tool, or a thermal process tool. The process tool may be configured as a cluster tool or a number of process modules coupled by a common handler.

The results of the inspection performed by the methods and systems described herein may be used to alter a parameter of a process or a process tool using a feedback control technique, a feedforward control technique, and/or an in situ control technique. The parameter of the process or the process tool may be altered manually or automatically.

The embodiments described herein may include any step(s) of any method(s) described in commonly assigned U.S. patent application Ser. No. 11/561,659 by Zafar et al. and Ser. No. 11/561,735 by Kulkarni et al., both of which were filed on Nov. 20, 2006, and both of which are incorporated by reference as if fully set forth herein. In addition, the embodiments of the system described herein may be further configured as described in these patent applications. Another embodiment relates to a method for detecting pinholes in a film formed on a wafer. The method includes generating output responsive to light from the wafer using an inspection system. The output includes first output corresponding to defects on the wafer and second output that does not correspond to the defects. Generating the output may be performed as described herein. In addition, the output, the first output, and the second output may include any of the output described herein. For example, in one embodiment, the second output includes output responsive to dark field background scattering from the film. The inspection system may be configured as described herein. For example, in one embodiment, the inspection system includes a dark field inspection system. In another embodiment, the light includes background scattered light detected using multiple channels of the inspection system. The multiple channels of the inspection system may include any of the channels described herein. The method also includes detecting the pinholes in the film formed on the wafer using the second output. Detecting the pinholes in the film may be performed as described further herein.

The embodiments described herein may be used for relatively rapid detection of pinholes in one or more films (or thin films) on monitor wafers using dark field background scattering analysis of output from one or more (or multiple channels) of an inspection system. However, the method and system embodiments may also be used for detection of pinholes in one or more films formed on product wafers. In addition, the embodiments described herein can be used for relatively rapid detection and analysis of pinhole formation in thin films on monitor wafers in a manufacturing environment. The films or thin films may include an oxide layer or any other films known in the art.

In one embodiment, the system and method embodiments are configured for the analysis of output responsive to multi-channel background light scattering (i.e., the "second output") acquired by a dark field inspection system. For example, generally, a dark field inspection system is configured to perform high pass filtering that allows light scattering signals that exceed a given signal-to-noise threshold to be collected for data analysis and defect classification. The embodiments described herein, however, may include the collection and quantitative analysis of those scattering signals that are excluded by the high pass filter.

In one embodiment, generating the output includes generating the output across substantially an entire surface of the wafer. Generating the output across substantially the entire surface of the wafer may be performed as described further herein. In one such embodiment, detecting the pinholes includes detecting the pinholes across substantially the entire surface of the wafer. In particular, since the output, and therefore the second output, can be generated across substantially the entire surface of the wafer, pinholes can be detected across substantially the entire surface of the wafer using such output. Therefore, the embodiments described herein can provide users with substantially complete background information about the wafer surface and the formation of pinholes.

In one embodiment, each of the pinholes is not detectable as a discrete object using the second output. For example, for the purposes of description herein, pinholes are generally defined by the formation of micro voids on any thermally produced thin films having a thickness of less than about 100 Angstroms. Each micro void is smaller than the spot size of the light beam of the inspection system that is incident on the wafer. Therefore, the pinhole is not detectable as a discrete object by the embodiments described herein. However, in some embodiments, detecting the pinholes includes determining a background light scattering signature using the second output and detecting the pinholes in the film formed on the wafer using the background light scattering signature. For example, when the micro voids are formed with a density such that numerous voids can be illuminated simultaneously by the inspection system (i.e., numerous voids are located within the area on the wafer defined by the incident illumination beam), the combined impact of the density and dimension of these micro voids creates a unique background light scattering signature that can be used to characterize the formation of pinholes.

In some embodiments, the output of the inspection system may be processed and analyzed on a localized area basis. For example, in one embodiment, detecting the pinholes includes detecting the pinholes in a localized surface area of the wafer using the second output. In one such embodiment, the localized surface area has an area approximately equal to an area of an incident beam of light of the inspection system on the wafer. For example, light scattering signals or output produced by a dark field inspection system may be processed holistically to provide substantially a whole wafer average or rough zonal information. The embodiments described herein can enhance the spatial resolution of data analysis by processing background light scattering information from relatively "tiny" localized surface areas that are characterized by the spot size of the incident light beam. In another embodiment, detecting the pinholes includes detecting the pinholes in localized surface areas of the wafer using the second output. In one such embodiment, the localized surface areas have areas approximately equal to an area of an incident beam of light of the inspection system on the wafer, and the localized surface areas extend across substantially an entire surface of the wafer. For example, each localized area may have a size equal to or less than about several square microns and may be aligned next to each other with respect to the wafer surface to cover substantially the entire wafer surface. In some embodiments, the method includes identifying one or more characteristics of the pinholes in localized surface areas of the wafer using the second output. In one such embodiment, the localized surface areas extend across substantially an entire surface of the wafer. For example, by analyzing the signals from each localized area individually, the embodiments enable detection of the location, size, and magnitude of pinhole clustering on any given area of the wafer surface. The location, size, and magnitude information may be provided to a user by the embodiments described herein.

In one embodiment, detecting the pinholes includes determining one or more power spectral density (PSD) curves using the second output and detecting the pinholes in the film formed on the wafer using the one or more PSD curves. For example, the embodiments may utilize unique differences in the PSD curves generated for wafers with varying levels of pinhole characteristics. In this manner, each level of pinhole formation (including no pinhole formation) may be characterized by a unique PSD curve. For example, given the density, width, and depth of pinhole formation in any thin film, the light scattering off of the surface will form a unique PSD curve. The PSD curves may be determined in any suitable manner using the second output.

In one embodiment, the method includes determining one or more parameters of the inspection system that can be used to generate the output such that the second output is sensitive to the pinholes. For example, for each PSD curve, the bands of frequencies that most consistently capture the differences in background light scattering due to pinhole formation can be identified. In one such example, based on experimental results, the PSD curves can be identified for wafers containing pinholes and wafers that do not contain pinholes that would diverge at designated frequency ranges covered by the narrow and wide channels of the dark field inspection system used in the embodiments described herein. Based on those bands of frequencies, the configurations of beam angles of incidence, collection channels, polarizations, and mask (i.e., one or more parameters) of the dark field inspection system can be determined that include frequency ranges that cover those PSD frequency bands of interest most optimally. In this manner, with those PSD curves, multi-channel metrics (or parameters) and thresholds may be identified for the detection and/or control of pinhole formation in any thin film. With the most optimal scan configurations applied on the dark field inspection system, the background light scattering data can be collected and analyzed as described herein. This data enables the creation of a matrix of statistical information that can be used to identify the overall characteristic of the pinhole formation.

In one embodiment, the method includes determining one or more characteristics of the pinholes as a function of position on the wafer using the second output. For example, since the background light scattering signals from multiple detection channels may be collected and analyzed for each localized surface area on the wafer, which may be characterized by the spot size of the illumination beam of the inspection system, the embodiments can be used to detect and quantify pinhole formation at each localized area throughout substantially the whole wafer surface. This capability enables identification of the location, size, and magnitude of any spatial pinhole conditions across the entire wafer surface. In contrast, in any other pinhole detection system or method, information about the pinhole formation is only detectable at the specific spot of measurement. However, the embodiments described herein may use substantially the whole wafer background scattering information to detect and quantify pinhole formation on substantially the entire wafer surface.

As described further above, the dark field inspection system used in the embodiments described herein may include narrow and wide channels. However, the embodiments described herein may also be applied on dark field inspection systems that have more than two light collection channels, which may or may not include narrow and wide channels. Such systems preferably have the ability to provide pixel level sub-particular light scattering data. With such systems, the sensitivity of the multiple channels to pinhole formation can be determined as described herein. The embodiments described herein may also include selecting sub-particular light scattering data from the most sensitive channels for ratio analysis or other analysis described herein.

In one particular example of the embodiments described herein, monitor wafers having a thermal oxide layer formed thereon may be scanned on the SP2 tool. The unique PSD characteristics due to pinhole formation may be identified. A channel of the system such as the wide channel configured to detect scattering of the normal incidence beam (the "normal wide channel") may be identified as the most sensitive channel of the inspection system to PSD changes. The relative change in output of this channel with respect to another channel of the system such as the narrow channel configured to detect scattering of the normal incidence beam (the "normal narrow channel") may be identified as the unique identifier of pinhole formation. Output responsive to the background light scattering signals may be obtained from the narrow and wide channels. The normal to wide (or vice versa) ratio may be analyzed for each localized area throughout substantially the entire wafer surface. Pinhole formation may be identified by comparing the measured ratio to predetermined ratios, which may be confirmed from PSD modeling.

In one embodiment, the method includes controlling pinhole formation in the film formed on the wafer by applying a threshold to the second output. In particular, since the second output is responsive to the pinholes formed in the film on the wafer, the second output may be thresholded in order to control pinhole formation. The threshold may be applied to the second output in any suitable manner. In addition, appropriate thresholds for this embodiment may be determined in any suitable manner. For example, second output corresponding to various levels of pinhole formation may be determined as described herein. As such, the second output corresponding to pinhole formation outside of process control limits may be determined and used to determine appropriate thresholds for this step.

In another embodiment, the method includes controlling pinhole formation in the film formed on the wafer by determining one or more characteristics of the pinholes in the film formed on the wafer using the second output and applying one or more thresholds to the one or more characteristics. The one or more characteristics of the pinholes may include any of the characteristics of the pinholes described herein. In this manner, the one or more characteristics of the pinholes may be thresholded in order to control pinhole formation. The threshold may be applied to the one or more characteristics of the pinholes in any suitable manner. In addition, appropriate thresholds for this embodiment may be determined in any suitable manner. For example, the one or more characteristics of the pinholes corresponding to various levels of pinhole formation may be determined as described herein. As such, the one or more characteristics of the pinholes corresponding to pinhole formation outside of process control limits may be determined and used to determine appropriate thresholds for this step.

Controlling the pinhole formation, in any of the embodiments described herein, may also include altering one or more parameters of a process tool used to perform a process on the wafer if the pinhole formation is determined to be outside of the process control limits. The one or more parameters of the process tool may be altered in any suitable manner (e.g., using a feedback control technique). The process tool may include any process tool that was used to perform a process on the wafer that may have contributed to the pinhole formation in the film formed on the wafer. For example, the process tool may include a thermal oxide growth process tool.

The embodiments described herein for detecting pinholes in a film formed on a wafer have a number of advantages over other methods and systems for detecting pinholes. For example, the embodiments provide relatively fast pinhole detection. In particular, it takes less than one minute per wafer to scan the surface of a wafer using a dark field inspection system described herein. This length of time is substantially fast compared to the more than about thirty minutes that it takes to manually search for pinholes using a SEM or AFM. In addition, the embodiments provide substantially precise and substantially accurate measurements. For example, using a 360 degree light scattering collector and suitable data processing, the unpatterned dark field inspection systems described herein collect background light scattering for each localized area with higher accuracy and precision than can be manually accomplished using a SEM or AFM. Furthermore, the embodiments described herein can be used to provide information for substantially the whole wafer. In contrast, all existing techniques for pinhole detection and analysis require the measurement of a wafer at a designated location. The embodiments described herein, however, can be used to provide substantially whole wafer information thereby enabling identification of pinhole defects on any region of the wafer. Moreover, the embodiments described herein can be used with thresholding for one or more predetermined pinhole defect characteristics. For example, the identification of multi-channel parameters for the quantification of pinhole formation, which may be performed as described herein, allows thresholds to be determined for SPC. The embodiments described herein expand the users' process visibility, and enables them to establish control over certain multi-channel parameters for pinhole control in a thin film of interest. Additionally, pinhole formation on critical gate oxide and dielectric layers is a key device killer that can result in millions of dollars in yield loss per year for an integrated circuit (IC) fab. Until now, there has been no method or system for the rapid detection of pinholes in a manufacturing environment. Application of the embodiments described herein will lead to rapid detection and resolution of pinhole formation in a manufacturing environment thereby resulting in substantial yield savings for IC manufacturers.

Each of the embodiments of the method described above may include any other step(s) of any other method(s) described herein. Furthermore, each of the embodiments of the method described above may be performed by any of the systems described herein.

An additional embodiment relates to a computer-implemented method for detecting pinholes in a film formed on a wafer. This method includes acquiring output responsive to light from the wafer generated by an inspection system. The output includes first output corresponding to defects on the wafer and second output that does not correspond to the defects. Acquiring the output may be performed as described herein. In addition, the output, the first output, and the second output may include any of the output described herein. For example, in one embodiment, the second output includes output responsive to dark field background scattering from the film. The inspection system may be configured as described herein. For example, in one embodiment, the inspection system includes a dark field inspection system. The method also includes detecting the pinholes in the film formed on the wafer using the second output. Detecting the pinholes in the film may be performed as described further herein. Each of the embodiments of the method described above may include any other step(s) of any other method(s) described herein. Furthermore, each of the embodiments of the method described above may be performed by any of the systems described herein. Moreover, each of the embodiments of the computer-implemented method described above may be implemented as described herein.

A further embodiment relates to a system configured to detect pinholes in a film formed on a wafer. The system includes an inspection subsystem configured to illuminate the wafer and to generate output responsive to light from the wafer. The output includes first output corresponding to defects on the wafer and second output that does not correspond to the defects. The inspection subsystem may be configured as described herein. For example, the inspection subsystem may be configured to illuminate the wafer and to generate output responsive to light from the wafer as described herein. In addition, in one embodiment, the inspection subsystem includes a dark field inspection system. The output, the first output, and the second output may include any of the output described herein. For example, in one embodiment, the second output includes output responsive to dark field background scattering from the film. The system also includes a processor configured to detect the pinholes in the film formed on the wafer using the second output. The processor may be further configured as described herein. For example, the processor may be configured to detect the pinholes in the film as described further herein. Each of the system embodiments described above may be further configured as described herein.

Another embodiment relates to a method for monitoring a thermal process tool. The thermal process tool may include any of the thermal process tools described herein or any other thermal process tool known in the art. The method includes generating output responsive to light from a wafer using an inspection system. The output includes first output corresponding to defects on the wafer and second output that does not correspond to the defects. Generating the output may be performed as described herein. The inspection system may be configured as described herein. For example, in one embodiment, the inspection system includes a dark field inspection system. The output, the first output, and the second output may include any of the output described herein. For example, in one embodiment, the second output includes output responsive to dark field background scattering from the wafer. The wafer was processed by the thermal process tool prior to generating the output. The wafer may be processed by the thermal process tool in any manner known in the art. The method also includes monitoring the thermal process tool using the second output. Monitoring the thermal process tool may be performed as described further herein. Each of the embodiments of the method described above may include any other step(s) of any other methods described herein. Furthermore, each of the embodiments of the method described above may be performed by any of the systems described herein.

An additional embodiment relates to a computer-implemented method for monitoring a thermal process tool. The thermal process tool may include any of the thermal process tools described herein or any other thermal process tool known in the art. The method includes acquiring output responsive to light from a wafer generated by an inspection system. Acquiring the output may be performed as described herein. The inspection system may be configured as described herein. For example, in one embodiment, the inspection system includes a dark field inspection system. The output includes first output corresponding to defects on the wafer and second output that does not correspond to the defects. The output, the first output, and the second output may include any of the output described herein. For example, in one embodiment, the second output includes output responsive to dark field background scattering from the wafer. The wafer was processed by the thermal process tool prior to acquiring the output. The wafer may be processed by the thermal process tool in any manner known in the art. The method also includes monitoring the thermal process tool using the second output. Monitoring the thermal process tool may be performed as described herein. Each of the embodiments of the method described above may include any other step(s) of any other method(s) described herein. Furthermore, each of the embodiments of the method described above may be performed by any of the systems described herein. Moreover, each of the embodiments of the computer-implemented method described above may be implemented as described herein.

A further embodiment relates to a system configured to monitor a thermal process tool. The thermal process tool may include any of the thermal process tools described herein or known in the art. The system includes an inspection subsystem configured to illuminate the wafer and to generate output responsive to light from the wafer. The output includes first output corresponding to defects on the wafer and second output that does not correspond to the defects. The inspection subsystem may be configured as described herein. For example, the inspection subsystem may be configured to illuminate the wafer and to generate output responsive to light from the wafer as described herein. In addition, in one embodiment, the inspection subsystem includes a dark field inspection system. The output, the first output, and the second output may include any of the output described herein. For example, in one embodiment, the second output includes output responsive to dark field background scattering from the wafer. The wafer was processed by the thermal process tool prior to generation of the output by the inspection subsystem. The wafer may be processed by the thermal process tool in any manner known in the art. The system also includes a processor configured to monitor the thermal process tool using the second output. The processor may be further configured as described herein. For example, the processor may be configured to monitor the thermal process tool as described further herein. Each of the system embodiments described above may be further configured as described herein.

The embodiments described above generally relate to methods and systems for monitoring and/or controlling a semiconductor thermal process tool using output responsive to dark field background scattering (i.e., the "second output") from monitor wafers. However, the embodiments may be performed for product wafers or any other wafers known in the art. For example, the embodiments described herein can be used to control process variations inside a thermal processing chamber of a thermal process tool by monitoring the surface characteristic(s) of monitor wafers through the analysis of dark field background light scattering signals.

In this manner, the embodiments described herein may be performed by analyzing output responsive to background light scattering from the surface of monitor wafers using a dark field inspection system. These embodiments take advantage of the sensitivity of dark field inspection systems to background light scattering due to changes in surface characteristics of monitor wafers.

In one embodiment, the monitoring step includes determining one or more characteristics of a surface of the wafer using the second output. Determining one or more characteristics of the surface of the wafer using the second output may be performed as described further herein. In another embodiment, the monitoring step includes determining one or more characteristics of a surface of the wafer using the second output, and the one or more characteristics include roughness, granularity, or some combination thereof. For example, the roughness and granularity characteristics of a monitor wafer surface undergoing thermal processing will be directly impacted by parameters of the thermal process tool (e.g., furnace parameters) such as temperature and gas flow. However, the one or more characteristics of the surface of the wafer determined in these embodiments may also or alternatively include any other characteristics described herein.

In another embodiment, the monitoring step includes determining within wafer variation in one or more characteristics of a surface of the wafer using the second output. Determining the within wafer variation in one or more characteristics of the surface of the wafer using the second output may be performed as described further herein. In an additional embodiment, the monitoring step includes determining wafer-to-wafer variation in one or more characteristics of surfaces of the wafer and at least one additional wafer using the second output generated for the wafer and the at least one additional wafer. Determining wafer-to-wafer variation in the one or more characteristics of the surfaces of the wafer and at least one additional wafer using the second output generated for the wafer and the at least one additional wafer may be performed as described further herein. For example, parameters of the thermal process tool that vary within a thermal processing chamber may cause within wafer and wafer-to-wafer surface variations. Within wafer and wafer-to-wafer surface variations impact the characteristics of background scattering light from wafer surfaces such that unique scattering signals can be associated with specific surface characteristics.

Generally, a dark field inspection system is configured to perform high pass filtering to allow light scattering signals that exceed a given signal-to-noise threshold to be collected for data analysis and defect classification. The embodiments described herein, however, include the quantitative analysis of those scattering signals that are excluded by the high pass filter(s). For example, in one embodiment, the monitoring step includes determining one or more characteristics of the second output, which may be performed as described further herein, and determining one or more characteristics of a surface of the wafer based on the one or more characteristics of the second output, which may also be performed as described herein.

This method may be used to provide substantially complete background information about the wafer surface characteristic(s) as related to different process parameters of the thermal process tool. For example, in one embodiment, generating the output includes generating the output across substantially an entire surface of the wafer, which may be performed as described herein. In one such embodiment, the monitoring step includes determining one or more characteristics of a surface of the wafer across substantially the entire surface of the wafer, which may be performed as described further herein. For example, in some embodiments, output generated by a dark field inspection system responsive to light scattering from the wafer is processed to provide substantially a whole wafer average or rough zonal information.

In one embodiment, the monitoring step includes determining one or more characteristics of a localized surface area of the wafer using the second output, which may be performed as described herein. In one such embodiment, the localized surface area has an area approximately equal to an area of an incident beam of light of the inspection system on the wafer. The embodiments described herein can, therefore, enhance the spatial resolution of data analysis by processing output responsive to background light scattering from relatively "tiny" localized surface areas that may be characterized by the spot size of the beam incident on the wafer used for inspection. In another embodiment, the monitoring step includes determining one or more characteristics of localized surface areas of the wafer using the second output, which may be performed as described further herein. In one such embodiment, the localized surface areas have areas approximately equal to an area of an incident beam of light of the inspection system on the wafer, and the localized surface areas extend across substantially an entire surface of the wafer. For example, each localized area may have a size of about several square microns or less and may be aligned next to each other with respect to the wafer to cover substantially the entire wafer surface. In an additional embodiment, the monitoring step includes determining one or more characteristics of individual pixels on the wafer using the second output, which may be performed as described further herein. In one such embodiment, the individual pixels extend across substantially an entire surface of the wafer. For example, by analyzing the signals from each pixilated area individually, the embodiments enable detection of the impact of parameter (s) of the thermal process tool at a specific wafer position. Such detection of the impact can be used to translate pixilated scattering information into pixilated tool parametric information.

In addition, it is noted that the "individual pixels on the wafer" are not actually formed on the wafer. Instead, the "individual pixels" are individual photosensitive elements of the inspection system, each of which may detect light from the wafer and generate output responsive thereto. The output of the inspection, therefore, may include a substantial number of signals or data points, each of which corresponds to a position on the wafer at which the signal or data point was acquired. As such, the individual signals or data points in the output generated by the inspection system are also commonly referred to as "individual pixels." Since the locations on the wafer at which the individual signals or data points were generated can be determined by the inspection system or a processor coupled thereto, the "individual pixels on the wafer" can be defined as the individual signals or data points in output generated at different locations on the wafer.

In another embodiment, the monitoring step includes quantifying one or more changes in one or more characteristics of a surface of the wafer using the second output and identifying one or more magnitudes of the one or more changes due to one or more parameters of the thermal process tool. For example, by analyzing the output responsive to the background light scattering, the embodiments described herein can be used to quantify changes in surface characteristic(s) and to identify the magnitude of variations in the surface characteristic(s) due to specific parameters of the thermal process tool. Furthermore, in one embodiment, the monitoring step includes identifying one or more defects on a surface of the wafer using the second output, and the one or more defects are caused by variation in one or more parameters of the thermal process tool. For example, since the output responsive to the background light scattering is collected and analyzed for localized surface areas, each of which may be characterized by the spot size of the beam of the inspection system incident on the wafer, the embodiments enable the identification of spatial surface defects or anomalies as the result of parametric variations.

In one embodiment, the method includes determining one or more correlations between one or more parameters of the thermal process tool and the second output, which may be performed as described further herein. In another embodiment, the monitoring step includes determining one or more parameters of the thermal process tool corresponding to the second output, which may be performed as described further herein. In an additional embodiment, the monitoring step includes determining one or more characteristics of a surface of the wafer using the second output and determining one or more parameters of the thermal process tool corresponding to the one or more characteristics of the surface of the wafer, which may be performed as described further herein. For example, given the ability to analyze surface characteristic(s) of monitor wafers with respect to parametric variations, the embodiments can be used to translate output responsive to scattering from the wafer into quantitative results based on the measurement units of the parameters of the thermal process tool. Furthermore, correlation to one of the process parameters allows, for a relatively small process parameter region, to conveniently express any process variation in terms of variations in the one chosen parameter.

The embodiments described herein can also be used for single parameter expression of process variations. In particular, the embodiments enable the correlation of output responsive to background light scattering from monitor wafer surface(s) and different parameters of the thermal process tool. Given such a correlation, the embodiments also enable the cross correlation of different parameters of the thermal process tool to a characteristic of the background light scattering. As such, for a given range of parametric variations, one dominant parameter of the thermal process tool can be controlled to control the monitor wafer surface characteristic(s), and variations in the process can be expressed in terms of equivalent variations in the one dominant parameter of the thermal process tool.

For example, if all process parameters are fixed except for furnace temperature which is varied, the embodiments can be used to draw a direct correlation between output responsive to background light scattering and furnace temperature variations. Using this correlation with output generated at localized areas on the wafer that may be characterized by the spot size of the beam of the inspection system incident on the wafer, the embodiments can express localized scattering as equivalent localized temperatures. The localized temperatures can be used to conveniently generate output (e.g., color and/or contour plots) that provides an intuitive display of the actual furnace process variation across the surface of a wafer and among different wafers in terms of one parameter of interest.

In one embodiment, the monitoring step includes determining one or more characteristics of a surface of the wafer as a function of position on the wafer using the second output, which may be performed as described further herein. In one such embodiment, the monitoring step also includes determining variation in one or more parameters of the thermal process tool as a function of position on the wafer using the one or more characteristics, which may be performed as described further herein. Therefore, the embodiments described herein may provide substantially whole wafer data. In contrast, with any other thermal process tool parametric control methods, information about the monitor wafer surface is only detectable at specific spots of measurement or at limited locations inside the thermal process tool. The embodiments described herein, however, offer substantially complete wafer background scattering information, which can be used to detect and quantify the surface characteristic(s) as related to parameters of the thermal process tool anywhere on the surface of the monitor wafer.

In one embodiment, the method includes performing generating the output for more than one wafer processed simultaneously by the thermal process tool, which may be performed as described herein. In one such embodiment, the monitoring step includes determining variation in one or more parameters of the thermal process tool as a function of position of the more than one wafer within the thermal process tool during the process using the second output generated for the more than one wafer, which may be performed as described further herein. For example, substantially whole wafer temperature distribution information can be generated for all wafers processed through a thermal process tool, allowing users to gain complete visibility into the temperature variation across the entire processing zone of that thermal process tool. This analysis can also be duplicated for other parameters of the thermal process tool like gas flow. The results will provide a clear understanding of the impact of varying gas flow on monitor wafer surface characteristic(s) within the area of each wafer and across the entire process chamber of the thermal process tool.

The embodiments described herein can be used for applications such as learning and development of process control for thermal processing of materials such as polysilicon. However, the embodiments described herein can be equally viable and used for other wafer processes in which the relationship between surface characteristic(s) of the processed wafer and process tool parameters are important. For example, the embodiments may be used for the control of thermal processing of metal layers such as copper and tungsten. In each case, the fundamental approach as described herein is similar. The difference for each case may be the characteristic of the output generated by the inspection system for wafers processed by the different processes, since each process may produce wafers having unique background light scattering.

In one example of the above embodiments, the method may include scanning monitor wafers having polysilicon formed thereon on an inspection system such as the SP2 tool. The method also includes obtaining output responsive to the background light scattering for localized areas (e.g., each localized area) on the wafer surface. In addition, the method includes conducting localized background scattering signal and thermal process tool parametric analysis. The method further includes identifying process defects by comparing the background scattering to established thresholds. Alternatively, the background scattering can be converted or translated into temperature, gas density, or other parameters of the thermal process tool, and the result can be compared with established thresholds accordingly.

The embodiments described above provide a number of advantages over other methods and systems for monitoring and/or controlling a thermal process tool. For example, the embodiments described herein provide relatively fast substantially whole wafer surface characterization. For example, the embodiments described herein take less than about one minute per wafer to scan the surface of the wafer. In contrast, other methods and systems may take over about thirty minutes of multi-point measurements using a film metrology tool or AFM. In addition, the embodiments described herein provide substantially precise and substantially accurate measurements. For example, a dark field inspection system such as those described herein may use a 360 degree light scattering collector and suitable data processing to collect pixel level non-LPD light scattering output with far higher accuracy and far higher precision than can be manually accomplished using an AFM. Furthermore, the embodiments described herein provide direct wafer level measurements. For example, the embodiments identify the impact of parametric variation directly from the processed wafer surface. In contrast, thermocouples and gas flow meters do not have the ability to directly measure characteristic(s) of the wafer surface that can be used to determine one or more process parameters across the wafer. Moreover, the embodiments described herein provide substantially whole wafer information. In contrast, all existing techniques require the measurement of a wafer at a designated location, or measurement of just the thermal process tool environment. The embodiments described herein, however, provide substantially whole wafer information on a pixel level thereby enabling the identification of deviation due to parameters of the thermal process tool on any region of a wafer surface.

In one embodiment, the method includes controlling the thermal process tool using the second output, which may be performed as described further herein. In another embodiment, the method includes controlling one or more parameters of the thermal process tool by applying a threshold to the second output, which may be performed as described further herein. In an additional embodiment, the method includes controlling one or more parameters of the thermal process tool by determining one or more characteristics of a surface of the wafer using the second output and applying one or more thresholds to the one or more characteristics, which may be performed as described further herein. In this manner, the embodiments described herein can be used for thresholding of thermal process tool parameters based on the wafer surface characteristic(s). For example, the embodiments allow thresholds for one or more thermal process tool parameters to be determined based on wafer surface conditions.

In an additional embodiment, the method includes controlling one or more parameters of the thermal process tool across substantially an entire processing zone of the thermal process tool using the second output, which may be performed as described further herein. For example, the embodiments may be used to expand the end-users' process visibility and enables them to establish a control strategy over the entire processing zone of a thermal process tool.

Another advantage of the embodiments described herein is that the embodiments provide convenient single parameter expression of process variations. For example, the embodiments enable the correlation of output responsive to background light scattering from monitor wafer surfaces and different thermal process tool parameters. Give such correlation, the embodiments also enable the cross correlation of different thermal process tool parameters for a given background light scattering characteristic. As such, for a given range of parametric variations, one dominant thermal process tool parameter can be controlled for the control of the monitor wafer surface characteristic.

The control of surface roughness and granularity characteristics are critical elements of the latest technology nodes. By providing the capability for relatively rapid and substantially accurate identification of surface characteristic(s), the embodiments described herein will enable IC fabs to advance their control of thermal processing. The resulting improvement in product quality and yield would lead to multi-million dollar savings over current conditions.

Although embodiments are described herein with respect to monitoring and/or controlling a thermal process tool, it is to be understood that the embodiments may be used to monitor and/or control any other wafer fabrication tool known in the art. For example, the method and system embodiments may be used to monitor and/or control a deposition tool such as a CVD tool, a PVD tool, an atomic layer deposition tool, and an ECD tool, a CMP tool, an etch tool, or any other tool described herein or known in the art for which one or more parameters can be correlated to one or more characteristics of the wafers that can be determined as described herein.

As we progress to smaller and smaller design rules, process control is extending into a new realm. Crystal defects in substrates can affect gate performance. The thickness of gate oxides can be measured in terms of a few atomic layers. Interconnects are reaching dimensions in which resistance is dominated by single-grain scattering. In this environment, where nanometer and sub-nanometer surface topography variations can have important ramifications for device performance, light scattering can provide an Angstrom-sensitivity, substantially full-wafer map of microroughness variations at speeds of tens of wafers per hour. As described further herein, such microroughness maps correlate strongly with AFM measurements performed at discrete points on wafers. The sensitivity of light scattering inspection systems makes possible new development applications such as process window characterization for grain size of interconnect films, as well as unprecedented bare substrate microroughness characterization. The speed of inspection systems extends these applications into topographic excursion monitoring and process control as described further herein.

Previously, surface scattering was viewed mainly as a noise source for optical wafer inspection and therefore a limiting factor in particle detection sensitivity. At best, wafer manufacturers and their customers used surface scattering measurements called "haze" as a simple, single-value representation of surface quality, to accept or reject wafers. However, with the proper architecture and processing, an enhanced version of haze called "microhaze" can provide a wealth of information that is valuable for process development, and may even be used for process monitoring.

The system embodiments described herein are configured to leverage system architecture such as the system architecture of the SP2 unpatterned wafer inspection system to deliver surface-scattering data at unprecedented sensitivity. The measurement sensitivity of this system can be applied to detect changes in surface roughness for a variety of surface types. Sub-Angstrom changes in root-mean-square (RMS) surface roughness can be detected for relatively smooth front-end-of-line (FEOL) substrates and films. Excursions in grain size of rough interconnect films such as copper (Cu), tungsten (W), and polysilicon can be monitored using this technology. Experimental microhaze data for a Cu film described further herein confirms the theoretically predicted functional relationship between microroughness and scattering theory with a substantially high correlation coefficient.

The ability to effectively measure surface roughness variations over substantially the entire wafer surface that were previously undetected, or detected only with long measurement times or over substantially small sampling areas, overcomes current sensitivity and throughput barriers to topographic process window characterization in development, and topographic process window control in production.

As described further herein, the Surfscan SP2 scanning surface inspection system works by scanning a laser spot over the surface of a wafer with either normal or oblique incidence and collecting the scattered light into a narrow or wide collection channel. From that scattering signal, both LPDs and haze can be extracted. FIG. 3 described further above shows a simplified method for distinguishing an LPD from haze by applying a threshold. In particular, as described further above, FIG. 3 illustrates the wafer surface scattering signal plotted as a function of position on the wafer (or time). First output 20 includes relatively sharp peaks that represent distinct, localized defects commonly called LPDs. Second output 22 is the background signal that represents scattering from the surface on which the defects are found. LPDs can be separated from background scatter, or haze, by applying a threshold to the wafer surface scattering signal. The LPD information can be used to generate a map of localized defects, which is the predominant information gathered from a system of this sort.

The haze portion of the signal is often regarded as nuisance when localized defects are the aim of the measurement. As a result, grazing-angle systems that use sophisticated algorithms were designed to suppress haze, as described by Wayne MeMillan, "Surfscan SP2: Enabling Cost-Effective Production and the 65 nm Node and Beyond," *Yield Management Solutions*, Spring 2004, pp. 14-23, which is incorporated by reference as if fully set forth herein. Soon it was determined that haze maps also contain important information, because haze correlates with surface roughness. However, the value of haze information has been limited by lateral resolution and sensitivity, by the lack of haze standards, and by the visible wavelength employed by most unpatterned surface inspection systems.

To address these limitations and make best use of the information contained in the haze signal, the embodiments described herein were developed to provide a haze map of unprecedented resolution at an ultraviolet (UV) wavelength. These microhaze maps show surface-roughness, contaminants, residues, film morphology, and even film-thickness variations.

The relationship between haze and surface roughness is summarized here, and can be examined in more detail by consulting the literature such as C. Thomas Larson, "Measuring haze on deposited metals with light-scattering-based inspection systems," MICRO (September, 1996), John C. Stover, *Optical Scattering: Measurement and Analysis*, SPIE Optical Engineering Press, Bellingham, Wash. (1995), J. M. Elson, J. P. Rahn, and J. M. Bennett, *Applied Optics*, 22, 3207(1983), and B. W. Scheer, "Development of a physical haze and microroughness standard," SPIE Vol. 2862, pp. 78-95 (1996), which are incorporated by reference as if fully set forth herein. To begin, RMS roughness, σ (or sometimes $R_q$), is most simply described as:

$$\sigma = \lim_{L \to \infty} \frac{1}{L} \left( \int_{-L/2}^{L/2} [z(x) - <z>]^2 \, dx \right)^{1/2} \quad (1)$$

where L is the distance over which the measurement is taken, z(x) are the set of heights of data points collected at distances x, and <z> is the average height. This definition works very well when comparative measurements are limited to one type of measurement system, such as a profiler or an AFM, and measurement parameters (such as scan size and tip radius) are held constant. However, in discussion herein, widely different systems, in fact, a scanning surface inspection system and an AFM, are compared so a more general treatment of surface roughness is warranted.

Every wafer surface includes a continuum of features, with lengths (or spatial wavelengths) ranging from the distance between atoms to the size of the wafer. Equivalently, each surface can be described by a spectrum of spatial frequencies, PSD(f).

In this nomenclature, the RMS roughness for a given measurement system can be obtained by integrating the PSD as follows:

$$\sigma = \left( \int_{f_{\min}}^{f_{\max}} PSD(f) df \right)^{1/2} \quad (2)$$

where $f_{min}$ and $f_{max}$ describe the limits of the instrument used to measure the RMS roughness. (For the sake of simplification, but without loss of generality, we present here a one-dimensional description. In reality, one would integrate in two dimensions.)

Figure 8:
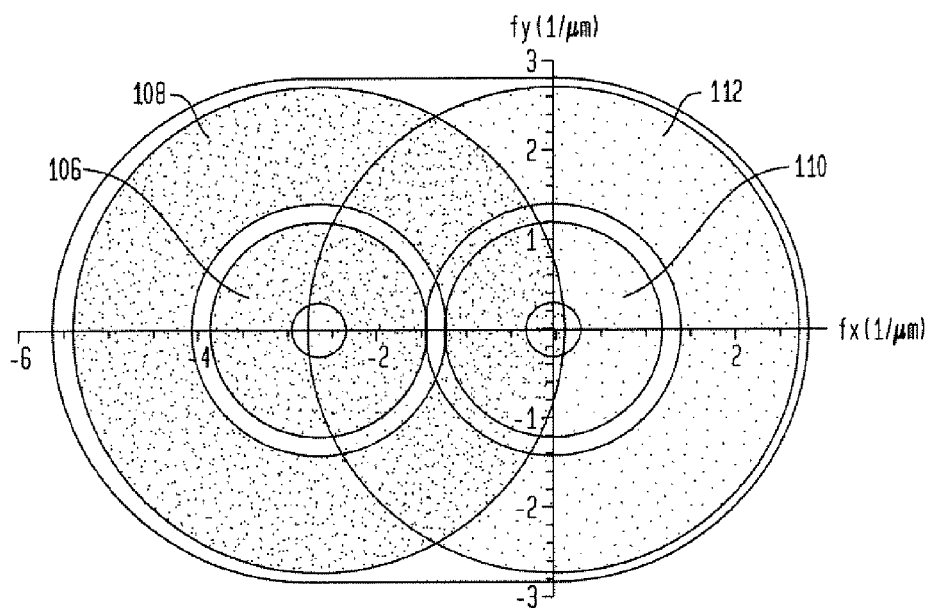
FIG. 8 is a schematic diagram illustrating spatial frequencies collected by a system embodiment described herein.

For a scanning surface inspection system, $f_{min}$ and $f_{max}$ can be found by relating the scattering angles to the spatial frequency through the grating equation:

$$f = \frac{\sin(\theta_s) - \sin(\theta_i)}{\lambda} \quad (3)$$

where $\theta_i$ and $\theta_s$ represent the angles of incidence and scattered light, and $\lambda$ is the wavelength of the light. In particular, the spatial frequencies encompassed by the system described above are shown in FIG. 8. For example, as shown in FIG. 8, spatial frequencies 106 are collected by the oblique incidence "narrow" channel, and spatial frequencies 108 are collected by the oblique incidence "wide" channel. In addition, spatial frequencies 110 are collected by the normal incidence "narrow" channel, and spatial frequencies 112 are collected by the normal incidence "wide" channel. Note that four channels are given, denoted "normal-wide," "normal-narrow," "oblique-wide," and "oblique-narrow." These channels correspond to the optical configuration of the system shown in FIG. 7. Each channel has a unique spatial bandwidth.

On the other hand, a surface profiler or an AFM has a lower frequency limit equal to the inverse length of the scan, $$f_{\min} = \frac{1}{L} \quad (4)$$

and an upper frequency limit given by the Nyquist criterion as $$f_{\max} = \frac{1}{2d} \quad (5)$$

where d is the sampling distance or the minimum resolution of the system, whichever is larger. (For the relatively large AFM scans taken herein, d is the sampling distance.) Thus, the spatial bandwidth of the AFM measurement will depend upon the scan size and the number of data points sampled per scan line.

Figure 9:
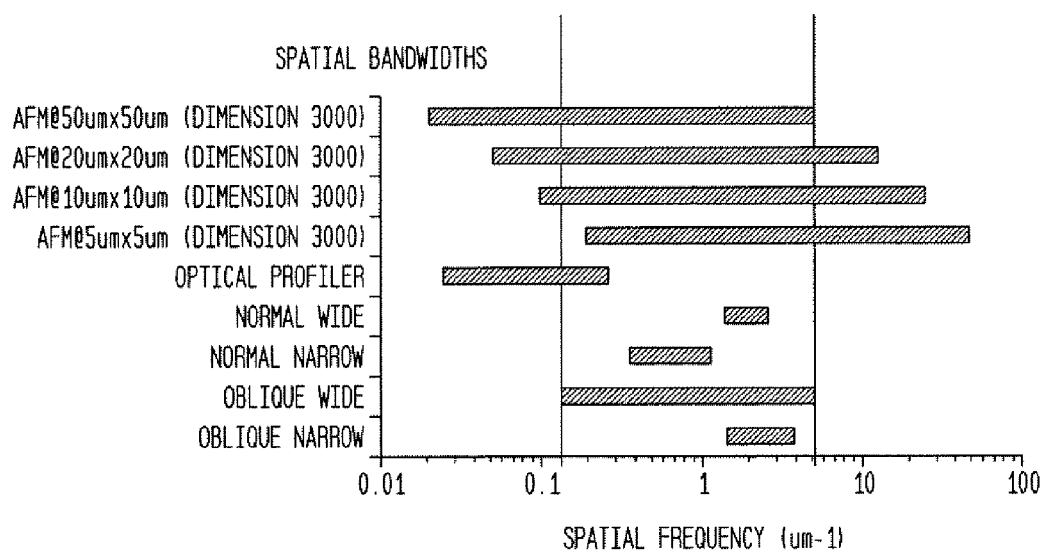
FIG. 9 is a schematic diagram illustrating a comparison of the spatial frequencies encompassed by a system embodiment described herein and an atomic force microscope (AFM)

Comparing the spatial frequencies encompassed by the system embodiments described herein and the AFM (a Park Scientific Instruments M5), as shown in FIG. 9, there is significant overlap between the spatial frequencies encompassed by the system embodiments described herein (labeled on the plot as Normal Wide, Normal Narrow, Oblique Wide, and Oblique Narrow) and the AFM especially with the Oblique-Wide channel of the system embodiments described herein. However, RMS roughness measurements by the two systems will correlate best when the data of both systems are filtered to include the same spatial bandwidth, that is, when the integration limits of Equation 2 are equal. The vertical lines in FIG. 9 indicate a possible band-pass filter, to compare the Oblique-Wide channel of the system embodiments described herein with a 10 μm or 20 μm scan of the AFM.

The relationship between haze, H, and RMS roughness, θ, is given by $$H = \left( \frac{4\pi \cos(\theta_i)}{\lambda} \right)^2 \cdot R_0 \sigma^2 \quad (6)$$

where $R_0$ represents the specular reflectance of the surface, and is a function of $\lambda$, $\theta_i$, and polarization of the incident light. Haze, then, varies as the square of the RMS roughness.

For a given surface inspection system ($\lambda$, $\theta_i$, $\theta_s$ and polarization held constant), the haze measurement should correlate well with the RMS roughness given by an AFM, as long as the two data sets are corrected by the appropriate band-pass filter to equalize their spatial frequency ranges. Several simplifications have been made in the discussion above. First, we have assumed that the collection of scattered light by the system optics is 100% efficient. In reality, a roll-off near the bandpass edges will occur, but this roll-off will not have a large effect on the results. Second, we have assumed that surface height variations are small with respect to the wavelength of light, which is the definition of microroughness, and which is a condition that is likely well satisfied by any bare or blanket-film wafers we might consider, given that the system embodiments may use an illumination wavelength of about 355 nm. Third, we have assumed that haze arises solely from microroughness effects. A counter example would apply if the system measures material transparent to UV radiation such as most dielectric films. If the beam penetrates the top surface of the material and reflects from underlying defects or interfaces, the haze measurement will include contributions from sub-surface scattering or thin film interference effects, not just from microroughness. This kind of haze can also be exploited for process control as described further herein.

The following example, and all other examples described herein, are not to be considered limiting embodiments of the invention and are included herein for example purposes only.

Figure 10:
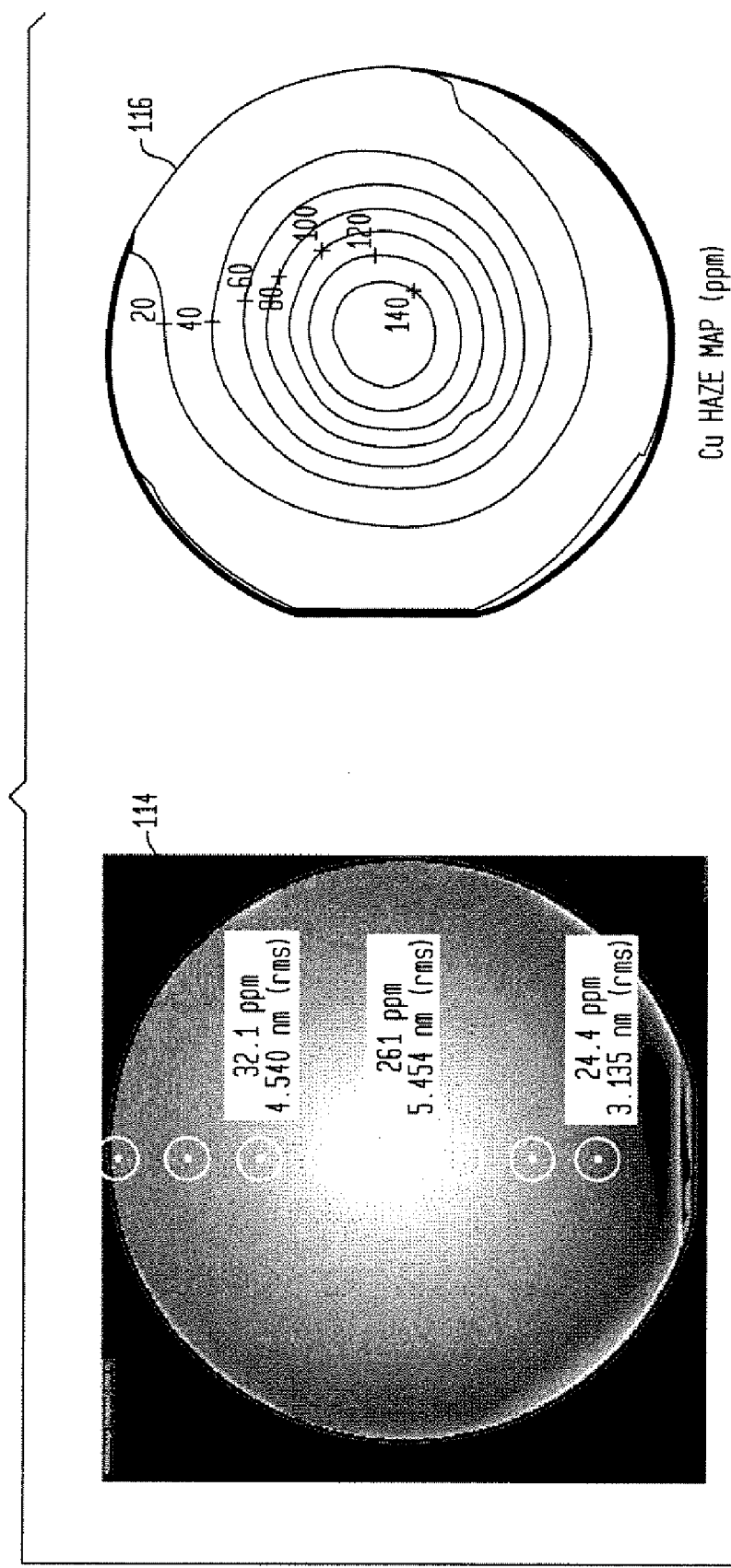
FIG. 10 is a schematic diagram illustrating an image of substantially an entire wafer having a copper film formed thereon generated by a system embodiment described herein and a contour haze map of the wafer.

To ensure best success in correlating microroughness with microhaze, for our first experiment, we chose a wafer that would be as immune to complicating effects as possible: a clean Cu film. The blanket Cu film was formed on the wafer by ECD. At 355 nm, the penetration depth of Cu is less than 15 nm, so haze should be a function of only the Cu film topography. In addition, this wafer shows an unusually large variation in grain size across its surface. FIG. 10 shows full-wafer image 114 of the Cu film wafer acquired by a system embodiment described herein, a data set that can be collected at a throughput of tens of wafers per hour, including overhead for wafer handling. Circled points on image 114 indicate locations where eight AFM scans were performed. FIG. 10 also includes contour haze map 116 for the same wafer. Output used to form image 114 and map 116 was obtained from the oblique wide channel of the system.

Figure 11B:
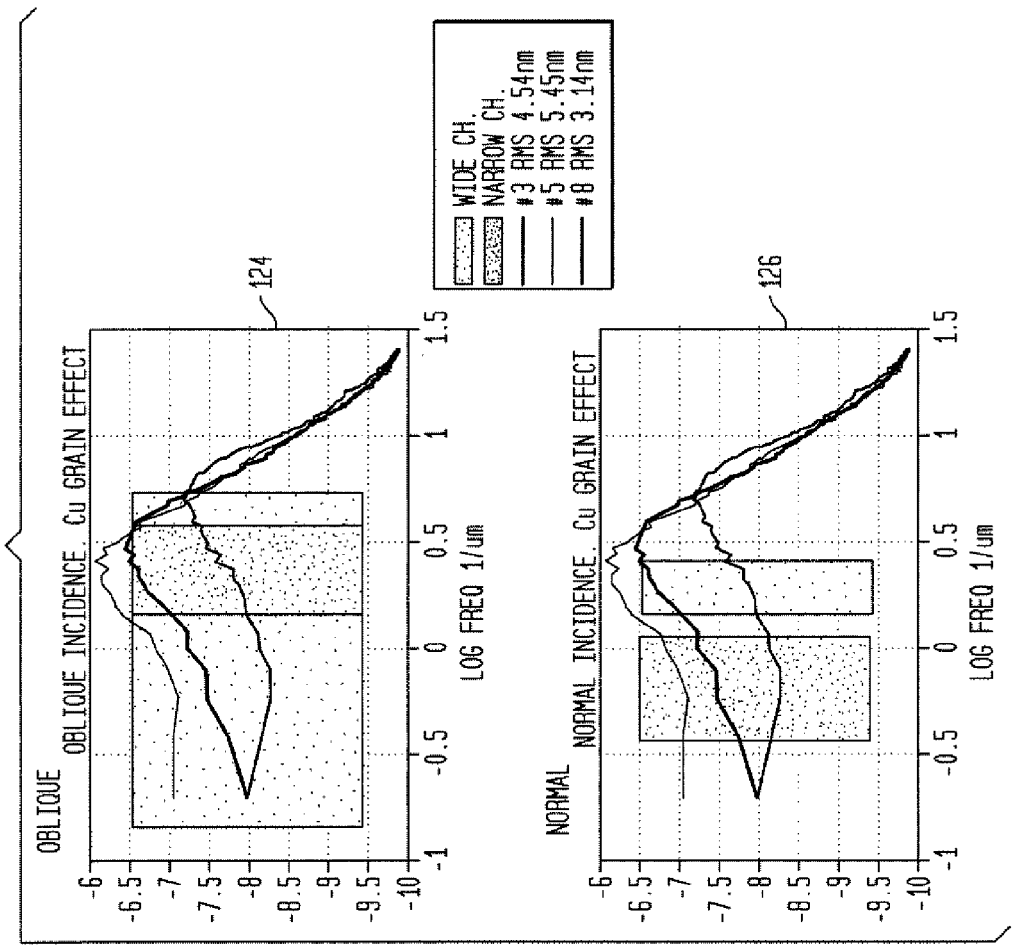
FIG. 11b includes plots of the power spectral densities (PSDs) of the AFM scans shown in FIG. 11a overlaid with the spatial frequency bands of various optical configurations of a system embodiment described herein.
Figure 11A:
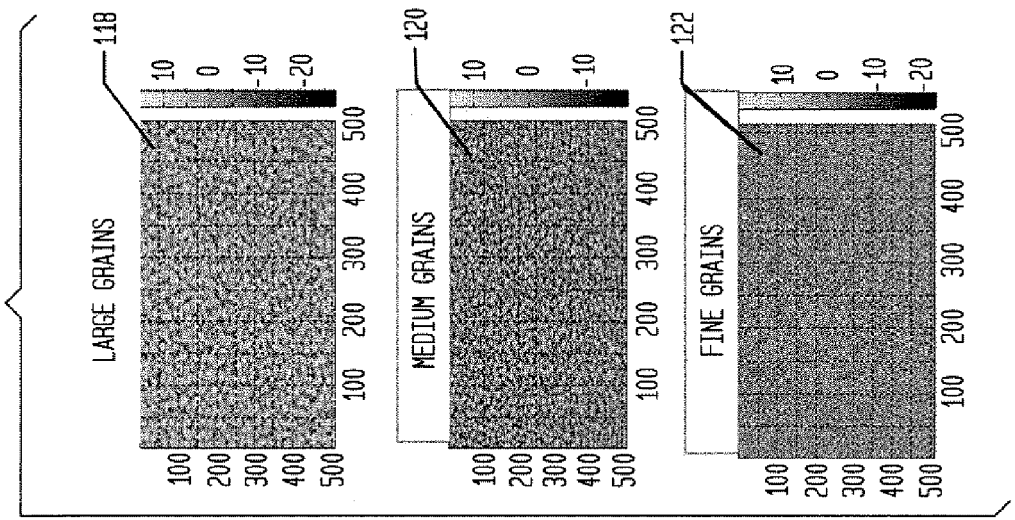
FIG. 11a includes representative AFM scans of the wafer of FIG. 10 with different grain sizes.

FIG. 11a includes three representative AFM scans of the wafer described above. AFM scan 118 is for large grain sizes. AFM scan 120 is for medium grain sizes, and AFM scan 122 is for fine grain sizes. Scans 118, 120, and 122 show significant variation in (MS roughness arising from grain size differences. We calculated PSDs from these scans and the other scans performed at the locations indicated on the wafer map in FIG. 10. The PSDs are shown in FIG. 11b, with spatial bandwidths of the inspection system optics overlaid. In particular, plot 124 shows the PSDs of the AFM scans overlaid with the spatial frequency bands of the oblique incidence system configuration with a wide collection channel and a narrow collection channel. Plot 126 shows the PSDs of the AFM scans overlaid with the spatial frequency bands of the normal incidence system configured with a wide collection channel and a narrow collection channel.

Figure 12:
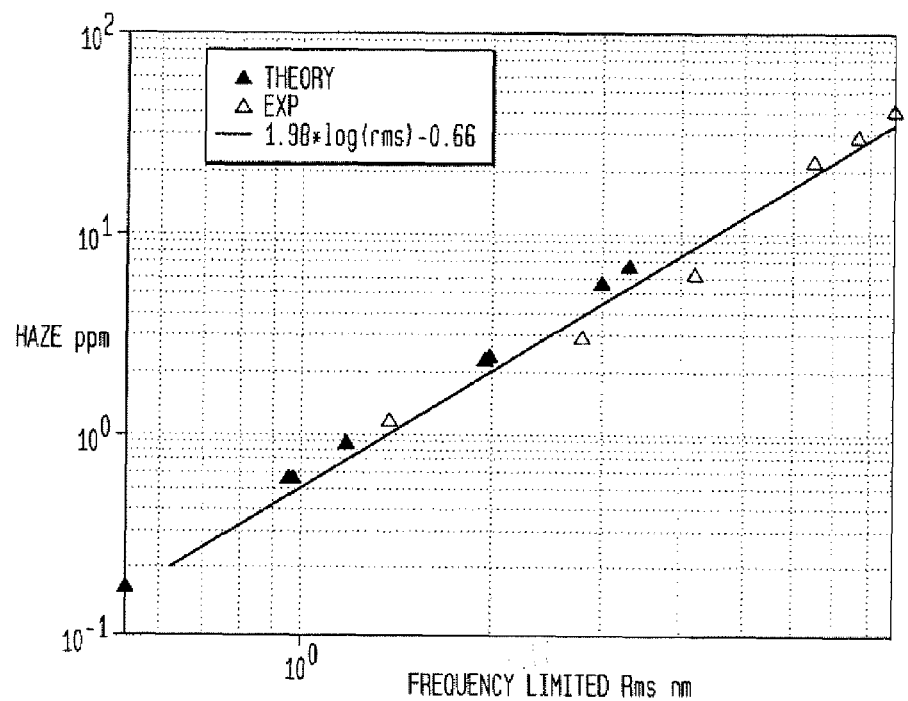
FIG. 12 is a plot showing frequency-matched microroughness squared values derived from AFM data compared to experimental haze values measured by the normal, wide channel of a system embodiment described herein.

We then calculated "frequency-matched" RMS roughness values from these PSDs, i.e. corrected to match the spatial bandwidths of the system (using Equation 2, with frequency values from FIG. 8). FIG. 12 compares the resulting frequency-matched microroughness values (squared) derived from the AFM data, with the experimental haze values measured by the normal-wide channel of the system. Note that no fitting parameters were used. The "theory" points shown in FIG. 12 are microhaze values predicted from Equation 6, based on the frequency-limited AFM data. The "exp" points shown in FIG. 12 are actual microhaze measurements at locations where AFM measurements were taken. Note that both the theoretical and experimental data agree well with a common best-fit line, which has a slope of 1.98 that is substantially close to the predicted value of 2.

In FIG. 12, the experimental data show some scatter, which we hypothesize can be attributed primarily to AFM measurement error such as tip convolution effects. (See, For example, J. E. Griffith, D. A. Grigg, M. J. Vasile, P. E. Russell and E. A. Fitzgerald, "Characterization of Scanning Probe Tips for Linewidth Measurement," *J. Vac. Sci. Technol. B* 9(6), November/December 1991, pp. 3586-3589, which is incorporated by reference as if fully set forth herein). These results show that, for conducting films, a substantially strong correlation exists between microhaze measurements and frequency-matched AFM measurements of RMS roughness.

Figure 13:
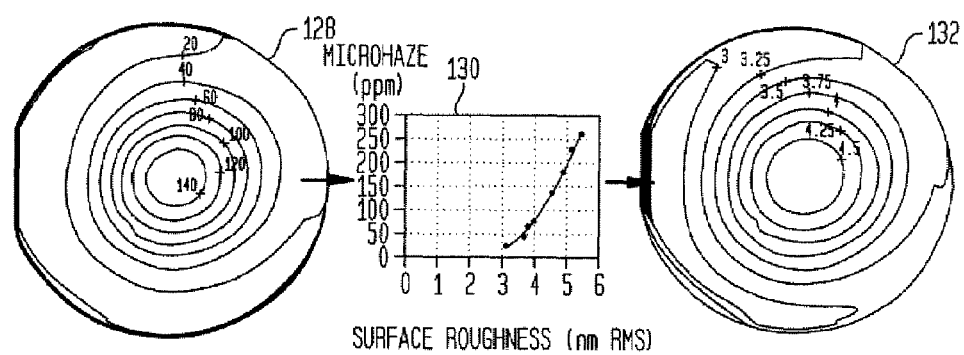
FIG. 13 is a schematic diagram illustrating a contour map of microhaze and a contour map of microroughness determined using the contour map of microhaze and a correlation between microhaze and microroughness.

The correlation between the frequency-matched RMS roughness and the measured haze value can be used to construct a microroughness map of the wafer. For example, as shown in FIG. 13, contour map 128 of microhaze and correlation 130 between microhaze and the frequency-matched RMS roughness can be used to construct contour map 132 of microroughness (in nm RMS) for a blanket Cu film. The translation from microhaze to microroughness is accomplished by applying the microhaze-to-roughness correlation as indicated in FIG. 13. This output is acquired from the oblique wide channel. The symbols in the correlation plot are "theory" microhaze values generated from Equation 6 and using the AEM data points indicated in FIG. 10. This data is analogous to the symbols shown in FIG. 11 except that the data is calculated for the oblique wide channel.

For metal films of interest, such as Cu, aluminum, and W, microroughness is dominated by grain size. FIG. 11*b* shows that the collection frequencies overlay ideally with the broad peak in the PSD that indicates grain size distribution. Thus, the haze map may be uniquely suited to serving as a grain size measurement proxy. Grain size can affect the resistance of the interconnects, and ultimately, the speed of the IC device. Furthermore, grain size has been associated with IC reliability in metal films, and thus may also provide information useful for predicting the probability of circuit failures. Using the systems and methods described herein for generating a substantially full-wafer microroughness map, a process window may be determined for interconnect microroughness. Furthermore, the ability to generate these substantially full-wafer maps at a speed of tens of wafers per hour enables process monitoring for grain-size excursions. As such, using the embodiments described herein for high-speed generation of a substantially full-wafer microroughness map, a process window can be quickly determined for interconnect microroughness, and the process can be monitored for grain-size excursions. In this manner, the embodiments described herein will help ensure more consistent device performance.

In some embodiments, therefore, the methods described herein include determining a process window for a process to be performed on a wafer based on the characteristic of the wafer determined by the method. In another embodiment, the processor of the system embodiments described herein is configured to determine a process window for a process to be performed on a wafer based on a characteristic determined by the processor as described herein.

The relationship between haze and microroughness described above may also be examined for polysilicon films as well as substrates. For polysilicon, microroughness affects electron-hole mobility, and a similarly strong correlation between frequency-matched AFM microroughness and haze has been measured. The microhaze data deviates from the AFM results most markedly at the low-frequency end of the spectrum. Taking a larger AFM scan may minimize this effect, which arises from edge effects. In this case, the broad collection angles of the collector described herein are preferable to establish a strong correlation between microhaze and microroughness.

The extension of this concept to monitoring the roughness of wafer substrate surfaces is more difficult, mainly because the surfaces are so much smoother than polysilicon surfaces, and the noise in the AFM measurements confounds the correlation to haze. (See, for example, Igor J. Malik, Krishna Vepa, Saeed Pirooz, Adrian C. Martin, and Larry W. Shrive, "Surface Roughness of Si Wafers: Correlating AFM and Haze Measurements," *Semiconductor Silicon/*1994: *Seventh International Symposium on Silicon Materials Science and Technology*, ed. H. R. Huff, W. Bergholz, and K. Surnino, The Electrochemical Society, Inc, PV 94-10, Pennington, N.J., 1994, p. 1182 and Egon Marx, Igor J. Malik, Yale E. Strasser, Thomas Bristow, Noel Poduje and John C. Stover, "Power spectral densities: A multiple technique study of different Si wafer surfaces," *J. Vac. Sci. Technol. B* 20(1), January/February 2002, pp. 31-41, which are incorporated by reference as if fully set forth herein.) The UV wavelength of the system embodiments described herein may be preferable for substrate microroughness measurements since a visible-wavelength beam would penetrate the top silicon layer of a silicon-on-insulator (SOI) substrate and complicate the measurement with non-topographic contributions.

The embodiments described herein have, therefore, a number of advantages over other currently used systems and methods. For example, as described further herein, the embodiments provide a new application of surface scattering using broad collection optics, UV illumination, and suitable algorithms to produce substantially full-wafer microhaze maps of Angstrom-level sensitivity and unprecedented lateral resolution, at a throughput of tens of wafers per hour. Therefore, the embodiments described herein may be immediately useful in applications in process development, and also hold potential for serving as a high speed, low cost process monitor.

As described further herein, laser scattering surface maps of polysilicon films were studied under a range of process conditions. The surface maps were shown to contain information that correlates with polysilicon film morphology impacting device performance within the CMOS process window for the 45 nm node. As described further herein, these surface maps can be used in embodiments of methods described herein for process tool monitoring that can enhance the fabrication line stability.

As described further above, laser surface scattering is responsive to surface roughness, and the resulting scattering signal in the absence of particles (traditionally called haze) is a sensitive measure of film morphology related to roughness. Tighter process control of film morphology is becoming increasingly important as advanced CMOS devices are produced at design rules of 45 nm and below. Unlike parameters such as film thickness, refractive index, and resistivity, which can be accurately and rapidly measured, surface properties such as microroughness are not commonly controlled in a production environment, due to the lack of fast and reliable metrology tools. Although AFM measurements can provide surface information, these instruments are not generally used in a production environment due to complex operation and low throughput. Laser scattering surface mapping can provide surface information over substantially the whole wafer surface at production-worthy throughputs for process monitor and/or control.

Further modifications and alternative embodiments of various aspects of the invention may be apparent to those skilled in the art in view of this description. For example, methods and systems for detecting pinholes in a film formed on a wafer or for monitoring and/or controlling a thermal process tool are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for detecting pinholes in a film formed on a wafer, comprising:
    generating output responsive to light from the wafer using an inspection system, wherein the output comprises first output corresponding to defects on the wafer and second output that does not correspond to the defects;
    wherein each of the pinholes is not detectable as a discrete object using the second output; and
    detecting the pinholes in the film formed on the wafer using the second output and not the first output.

2. The method of claim 1, wherein the second output comprises output responsive to dark field background scattering from the film.

3. The method of claim 1, wherein the inspection system comprises a dark field inspection system.

4. The method of claim 1, wherein the light comprises background scattered light detected using multiple channels of the inspection system.

5. The method of claim 1, wherein said generating comprises generating the output across substantially an entire surface of the wafer.

6. The method of claim 1, wherein said generating comprises generating the output across substantially an entire surface of the wafer, and wherein said detecting comprises detecting the pinholes across substantially the entire surface of the wafer.

7. The method of claim 1, wherein said detecting comprises determining one or more power spectral density curves using the second output and detecting the pinholes in the film formed on the wafer using the one or more power spectral density curves.

8. The method of claim 1, wherein said detecting comprises determining a background light scattering signature using the second output and detecting the pinholes in the film formed on the wafer using the background Tight scattering signature.

9. The method of claim 1, further comprising determining one or more parameters of the inspection system that can be used to generate the output such that the second output is sensitive to the pinholes.

10. The method of claim 1, wherein said detecting comprises detecting the pinholes in a localized surface area of the wafer using the second output, and wherein the localized surface area has an area approximately equal to an area of an incident beam of light of the inspection system on the wafer.

11. The method of claim 1, wherein said detecting comprises detecting the pinholes in localized surface areas of the wafer using the second output, wherein the localized surface areas have areas approximately equal to an area of an incident beam of light of the inspection system on the wafer, and wherein the localized surface areas extend across substantially an entire surface of the wafer.

12. The method of claim 1, further comprising determining one or more characteristics of the pinholes as a function of position on the wafer using the second output.

13. The method of claim 1, further comprising identifying one or more characteristics of the pinholes in localized surface areas of the wafer using the second output, wherein the localized surface areas extend across substantially an entire surface of the wafer.

14. The method of claim 1, further comprising controlling pinhole formation in the film formed on the wafer by applying a threshold to the second output.

15. The method of claim 1, further comprising controlling pinhole formation in the film formed on the wafer by determining one or more characteristics of the pinholes in the film formed on the wafer using the second output and applying one or more thresholds to the one or more characteristics.

16. A system configured to detect pinholes in a film formed on a wafer, comprising:
    an inspection subsystem configured to illuminate the wafer and to generate output responsive to light from the wafer, wherein the output comprises first output corresponding to defects on the wafer and second output that does not correspond to the defects;
    wherein each of the pinholes is not detectable as a discrete object using the second output; and
    a processor configured to detect the pinholes in the film formed on the wafer using the second output and not the first output.

* * * * *